United States Patent
Handa et al.

US009199218B2

(10) Patent No.: US 9,199,218 B2
(45) Date of Patent: Dec. 1, 2015

(54) WATER ABSORBING RESIN PARTICLES, METHOD FOR MANUFACTURING WATER ABSORBING RESIN PARTICLES, ABSORPTION BODY, ABSORPTIVE ARTICLE, AND WATER-SEALING MATERIAL

(75) Inventors: Masayoshi Handa, Himeji (JP); Kenji Tanimura, Himeji (JP); Atsushi Heguri, Osaka (JP); Yuichi Onoda, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 78 days.

(21) Appl. No.: 14/127,784

(22) PCT Filed: Jul. 23, 2012

(86) PCT No.: PCT/JP2012/068615
§ 371 (c)(1),
(2), (4) Date: Dec. 19, 2013

(87) PCT Pub. No.: WO2013/018571
PCT Pub. Date: Feb. 7, 2013

(65) Prior Publication Data
US 2014/0127510 A1 May 8, 2014

(30) Foreign Application Priority Data

| Aug. 3, 2011 | (JP) | 2011-170462 |
| Aug. 3, 2011 | (JP) | 2011-170466 |
| Aug. 3, 2011 | (JP) | 2011-170467 |
| Aug. 3, 2011 | (JP) | 2011-170471 |
| Aug. 3, 2011 | (JP) | 2011-170473 |
| Aug. 3, 2011 | (JP) | 2011-170477 |
| Sep. 30, 2011 | (JP) | 2011-218018 |
| Sep. 30, 2011 | (JP) | 2011-218028 |

(51) Int. Cl.

| C08F 2/32 | (2006.01) |
| B01J 20/26 | (2006.01) |
| C08J 3/12 | (2006.01) |
| A61L 15/26 | (2006.01) |
| A61L 15/28 | (2006.01) |
| A61L 15/48 | (2006.01) |
| A61L 15/60 | (2006.01) |
| C08J 3/075 | (2006.01) |
| C08F 220/06 | (2006.01) |

(52) U.S. Cl.
CPC ............... *B01J 20/261* (2013.01); *A61L 15/26* (2013.01); *A61L 15/28* (2013.01); *A61L 15/48* (2013.01); *A61L 15/60* (2013.01); *B01J 20/265* (2013.01); *C08F 2/32* (2013.01); *C08F 220/06* (2013.01); *C08J 3/075* (2013.01); *C08J 3/12* (2013.01); *C08J 2301/00* (2013.01); *C08J 2333/00* (2013.01); *Y10T 428/2982* (2015.01)

(58) Field of Classification Search
CPC . B01J 20/261; B01J 20/265; Y10T 428/2982; C08J 3/12; C08J 3/075; A61L 15/26; A61L 15/28; A61L 15/48; A61L 15/60; C08F 2/32; C08F 220/06
USPC ........... 428/402; 525/243; 526/200, 201, 202, 526/204, 207
See application file for complete search history.

(56) References Cited

FOREIGN PATENT DOCUMENTS

| CN | 1461317 | 12/2003 |
| CN | 1927914 | 3/2007 |
| EP | 1 714 985 | 10/2006 |
| JP | 56-131608 | 10/1981 |
| JP | 9-151224 | 6/1997 |
| JP | 10-251309 | * 9/1998 |
| JP | 11-267500 | 10/1999 |
| JP | 2006-068731 | * 3/2006 |
| WO | 97/03114 | 1/1997 |
| WO | 2006/025586 | 3/2006 |
| WO | 2006/033477 | 3/2006 |
| WO | 2011/065368 | 6/2011 |
| WO | 2011/078298 | 6/2011 |
| WO | WO2011/065368 | * 6/2011 |
| WO | 2012/053121 | 4/2012 |

OTHER PUBLICATIONS

Extended European Search Report issued for corresponding EP Application No. 12819365.3 on Feb. 18, 2015—10 pages.
Office Action issued in counterpart Chinese Application No. 201280037074.1 on Apr. 3, 2015—7 pages.

* cited by examiner

*Primary Examiner* — Leszek Kiliman
(74) *Attorney, Agent, or Firm* — Hamre, Schumann, Mueller & Larson, P.C.

(57) ABSTRACT

Disclosed is a water-absorbent resin particle in which the water-absorption rate of physiological saline is 1 second to 15 seconds, the median particle size is 100 μm to 600 μm, and the residual volatile component content is 1.5% by weight or less.

20 Claims, 3 Drawing Sheets

WATER ABSORBING RESIN PARTICLES, METHOD FOR MANUFACTURING WATER ABSORBING RESIN PARTICLES, ABSORPTION BODY, ABSORPTIVE ARTICLE, AND WATER-SEALING MATERIAL

TECHNICAL FIELD

The present invention relates to a water-absorbent resin particle, a method of producing a water-absorbent resin particle, an absorbent material, an absorbent article, and a water blocking material.

BACKGROUND ART

Water-absorbent resin particles have been used in hygienic materials such as disposable diapers and sanitary articles, agricultural materials such as water-retaining materials and soil conditioners, and industrial materials such as water blocking materials for cables and dew-catchers. In addition to these applications, the fields in which water-absorbent resin particles are applied have further expanded in recent years to include animal waste treatment materials such as pet sheets and toilet formulations for dogs or cats, portable toilets, air fresheners, absorbent drip sheets for meats and formulations for moisturizing cosmetics. Examples of the performance required by water-absorbent resin particles used in such applications include high water-absorption capacity, superior water-absorption rate and a suitable particle size corresponding to the application.

Among these applications, a comparatively large amount of body fluid and the like is expected to be discharged with considerable force onto water-absorbent resin particles used in applications which are special hygienic materials such as adult diapers, incontinence pads, toilet training pants and heavy day sanitary napkins, water blocking materials for cables, pet sheets, portable toilets and the like. Consequently, in above applications, emphasis has been placed on improvement of absorption capacity and absorption rate. Among these, although it is possible to accommodate absorption capacity by, for example, adjusting the amount of water-absorbent resin particles used, the absorption rate demonstrates a strong tendency to depend on unique properties of the water-absorbent resin particles. Consequently, various studies have been conducted thus far to achieve a superior water-absorption rate for water-absorbent resin particles.

For example, with respect to aqueous polymerization, a method has been disclosed for crosslinking the vicinity of the surface of a porous resin obtained in the presence of a foaming agent (see Patent Literature 1).

In addition, with respect to reversed-phase suspension polymerization, a method is disclosed in which an acrylic acid/acrylate aqueous solution is suspended in an alicyclic or aliphatic hydrocarbon solvent in the presence of a surfactant having an HLB value of 8 to 12 followed by carrying out reversed-phase suspension polymerization on the acrylic acid/acrylate (see Patent Literature 2), while another method is disclosed in which a water-soluble ethylenically unsaturated monomer is polymerized in the presence of a water-absorbent resin having a different water-absorption rate (see Patent Literature 3).

CITATION LIST

Patent Literature

[Patent Literature 1] WO97/3114
[Patent Literature 2] Japanese Patent Application Laid-open No. S56-131608
[Patent Literature 3] Japanese Patent Application Laid-open No. H9-151224

SUMMARY OF INVENTION

Technical Problem

In addition, an example of a method typically used to improve the water-absorption rate of water-absorbent resin particles consists of reducing the particle size of the water-absorbent resin particles. However, when the particle size of water-absorbent resin particles is reduced, fluidity becomes poor and handling ease of the particles tends to become difficult. Accordingly, a method is sought that enhances the water-absorption rate of water-absorbent resin particles while retaining suitable particle size.

Here, according to a study conducted by the inventors of the present invention, the water-absorbent resin particle disclosed in WO 97/3114 was unable to satisfy requirements for both particle size and water-absorption rate. In addition, according to a study conducted by the inventors of the present invention, although the water-absorbent resin particles disclosed in Japanese Patent Application Laid-open No. S56-131608 and Japanese Patent Application Laid-open No. H9-151224 have a comparatively large particle size and have superior handling ease and water-absorption rate, since the hydrocarbon dispersion medium used when producing the particles remains within the particles in the form of a volatile component, for example, a foul odor is generated following water absorption. As a result, there is the possibility that the odor generated during use of products containing the water-absorbent resin particles impairs the comfort of users (such as wearers). In addition, the amount of residual volatile components is also desired to be low from the viewpoints of consideration for the production process environment and improvement of water absorption.

Therefore, in one aspect thereof, a primary object of the present invention is to provide a water-absorbent resin particle which has superior handling ease, inhibits the generation of odor following water absorption and has a superior water-absorption rate, a water-absorbent material, a water-absorbent article and a water blocking material.

In another aspect thereof, a primary object of the present invention is to provide a method that enables the production of a water-absorbent resin particle that has superior handling ease, has a superior water-absorption rate, and has a low residual volatile component content.

Solution to Problem

The present invention provides a water-absorbent resin particle in which a water-absorption rate of physiological saline is 1 second to 15 seconds, a median particle size is 100 μm to 600 μm, and a residual volatile component content is 1.5% by weight or less.

The above-mentioned water-absorbent resin particle has superior handling ease because it has a particle size of a suitable size, inhibits the generation of odor following water absorption, and has a superior water-absorption rate.

The above-mentioned water-absorbent resin particle may have a specific surface area of 0.08 m$^2$/g or more. The water-absorption rate of the water-absorbent resin particle can be further improved by making the specific surface area to be within this range.

The above-mentioned water-absorbent particle may have a water-absorption capacity of the physiological saline of 30 g/g to 90 g/g.

In another aspect thereof, the present invention provides a method of producing a water-absorbent resin particle. The method according to the present invention may include in the following order, a first polymerization step including obtaining a suspension containing a water-containing gelated polymer by polymerizing a water-soluble ethylenically unsaturated monomer in a suspension which contains an oily liquid containing a hydrocarbon dispersion medium, a first aqueous liquid containing an aqueous solvent, the water-soluble ethylenically unsaturated monomer and a radical polymerization initiator, and a surfactant having an HLB value of 6 or higher, and in which the first aqueous liquid is dispersed in the oily liquid; and a second polymerization step including mixing a suspension containing the water-containing gelated polymer at 45° C. or higher with a second aqueous liquid containing an aqueous solvent, a water-soluble ethylenically unsaturated monomer and a radical polymerization initiator, and polymerizing the water-soluble ethylenically unsaturated monomer in a suspension in which the second aqueous liquid is further dispersed.

A water-absorbent resin particle obtained by the above-mentioned method has a superior water-absorption rate. Moreover, since the water-absorbent resin particle obtained by the above-mentioned method has a particle size of a suitable size, it has superior handling ease, and since it also has a low residual volatile component content, it is able to diminish the problem of the generation of a foul odor following water absorption.

In the above-mentioned second polymerization step, the temperature of the suspension in which the second aqueous liquid has been further dispersed at the time of completion of mixing of the suspension with the second aqueous liquid may be 35° C. or higher.

The residual volatile component content can be further reduced by making the temperature of the suspension at the time of completion of mixing of the second aqueous liquid to be within the above-mentioned range.

In the above-mentioned first polymerization step, the oily liquid may contain 50 parts by weight to 650 parts by weight of the hydrocarbon dispersion medium relative to 100 parts by weight of the water-soluble ethylenically unsaturated monomer contained in the first aqueous liquid.

The present invention also relates to a method of producing a water-absorbent resin particle provided with a polymerization step including polymerizing a water-soluble ethylenically unsaturated monomer in a suspension which contains an oily liquid containing a hydrocarbon dispersion medium and an aqueous liquid containing an aqueous solvent and the water-soluble ethylenically unsaturated monomer, the aqueous solvent containing water, and in which the aqueous liquid is dispersed in the oily liquid. The aqueous liquid has a viscosity of 20 mPa·s or more at 20° C. The suspension further contains a surfactant having an HLB value of 6 or higher.

A water-absorbent resin particle obtained by the above-mentioned method has a superior water-absorption rate. Moreover, since a water-absorbent resin particle obtained by the above-mentioned method has a particle size of a suitable size, it has superior handling ease, and since it has a low residual volatile component content, it is able to diminish the problem of the generation of a foul odor following water absorption.

The above-mentioned aqueous liquid may further contain a water-soluble thickener. The water-soluble thickener may contain at least one type of compound selected from hydroxyalkyl celluloses, hydroxyalkyl alkyl celluloses and carboxyalkyl hydroxyalkyl celluloses.

The residual volatile component content of the resulting water-absorbent resin particle can be further reduced as a result of the aqueous liquid containing the specific water-soluble thickener described above.

The present invention also provides a water-absorbent resin particle obtainable by the above-mentioned method, wherein
(1) a water-absorption capacity of physiological saline is 30 g/g to 90 g/g,
(2) a median particle size is 100 μm to 600 μm,
(3) a water-absorption rate of the physiological saline is 1 second to 20 seconds,
(4) an equilibrium swelling capacity is 20 mm or more, and
(5) a residual volatile component content is 1.5% by weight or less.

The above-mentioned water-absorbent resin particle has superior handling ease because it has a particle size of a suitable size, inhibits the generation of odor following water absorption, and has a superior water-absorption rate.

The present invention also relates to a method including a polymerization step including polymerizing a water-soluble ethylenically unsaturated monomer in a suspension which contains an oily liquid containing a hydrocarbon dispersion medium and an aqueous liquid containing an aqueous solvent and the water-soluble ethylenically unsaturated monomer, the aqueous solvent containing water, and in which the aqueous liquid is dispersed in the oily liquid.

The aqueous liquid further contains a hydrophilic polymeric dispersion agent. The suspension further contains a surfactant having an HLB value of 6 or higher.

A water-absorbent resin particle obtained by the above-mentioned method has a superior water-absorption rate. Moreover, since a water-absorbent resin particle obtained by the above-mentioned method has a particle size of a suitable size, it has superior handling ease. In addition, since the residual volatile component content of the water-absorbent resin particle is low, the problem of the generation of odor following water absorption can be diminished.

The above-mentioned hydrophilic polymeric dispersion agent may contain at least one type of compound selected from the group consisting of polyvinyl alcohol, polyvinylpyrrolidone, polyethylene glycol, polypropylene glycol and polyglycerol.

The aqueous liquid may contain 0.001 parts by weight to 10 parts by weight of the hydrophilic polymeric dispersion agent relative to 100 parts by weight of the water-soluble ethylenically unsaturated monomer.

The present invention also provides a water-absorbent resin particle obtainable by the above-mentioned method, wherein
(1) a water-absorption capacity of physiological saline is 30 g/g to 90 g/g,
(2) a median particle size is 100 μm to 600 μm,
(3) a water-absorption rate of the physiological saline is 1 second to 20 seconds,
(4) an equilibrium swelling capacity is 20 mm or more, and
(5) a residual volatile component content is 1.5% by weight or less.

The above-mentioned water-absorbent resin particle has superior handling ease because it has a particle size of a suitable size, inhibits the generation of odor following water absorption, and has a superior water-absorption rate.

The above-mentioned surfactant may contain at least one type of compound selected from the group consisting of sorbitan fatty acid esters, polyglycerol fatty acid esters and sucrose fatty acid esters.

As a result of the suspension containing the specific surfactant described above, the state of a W/O type reversed-phase suspension formed by a continuous phase in the form of the oily liquid (O) and a discontinuous phase in the form of the aqueous liquid (W) is more favorable, and a preferable form of water-absorbent resin particle tends to be easily obtained at a preferable particle size.

The above-mentioned water-soluble ethylenically unsaturated monomer may contain at least one type of compound selected from the group consisting of acrylic acid and a salt thereof, methacrylic acid and a salt thereof, and acrylamide.

The above-mentioned hydrocarbon dispersion medium may contain at least one type of compound selected from the group consisting of chain aliphatic hydrocarbons having 6 to 8 carbon atoms and alicyclic hydrocarbons having 6 to 8 carbon atoms.

In addition, the present invention also provides an absorbent material comprising the above-mentioned water-absorbent resin particle and hydrophilic fibers.

Moreover, the present invention further provides an absorbent article provided with a liquid-permeable sheet, a liquid-impermeable sheet and the above-mentioned absorbent material, wherein the absorbent material is arranged between the liquid-permeable sheet and the liquid-impermeable sheet that are arranged facing each other.

In addition, the present invention further provides a water blocking material provided with a first liquid-permeable sheet, a second liquid-permeable sheet and the above-mentioned water-absorbent resin particle, wherein the water-absorbent resin particle is arranged between the first liquid-permeable sheet and the second liquid-permeable sheet that are arranged facing each other.

Advantageous Effects of Invention

The water-absorbent resin particle of the present invention is able to have a superior water-absorption rate. Moreover, the water-absorbent resin particle of the present invention has superior handling ease because it has a particle size of a suitable size, and is able to diminish the problem of the generation of a foul odor following water absorption.

The water-absorbent resin particle obtained by the production method of the present invention is able to have a superior water-absorption rate. Moreover, since the water-absorbent resin particle obtained by the method of the present invention has a particle size of a suitable size, it has superior handling ease. In addition, since the residual volatile component content of the water-absorbent resin particle obtained by the method of the present invention is low, it is able to diminish the problem of the generation of a foul odor following water absorption.

DESCRIPTION OF EMBODIMENTS

Figure 1:
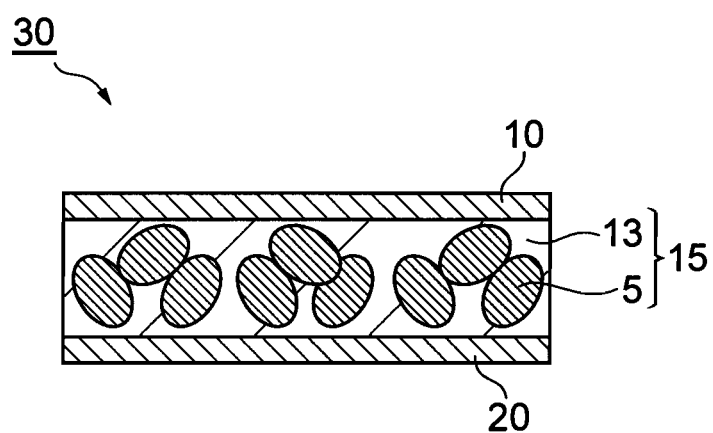
FIG. 1 is a cross-sectional view showing an embodiment of an absorbent article.

The following provides an explanation of embodiments of the present invention. However, the present invention is not limited to the following embodiments. All configurations described in the present description can be arbitrarily combined within a range that does not deviate from the purport of the present invention. For example, ranges of numerical values relating to various properties can be defined by using an upper limit value and lower limit value of a range of numerical values described in the present description, along with numerical values arbitrarily selected from numerical values described in the examples, for the upper limit value or lower limit value.

The water-absorption rate of physiological saline of the water-absorbent resin particle according to the present embodiment may be 1 second to 15 seconds or 1 second to 20 seconds. As a result of making the water-absorption rate to be within the above-mentioned range, or in other words, as a result of the water-absorbent resin particle having such a superior water-absorption rate, the water-absorbent resin particle is able to effectively prevent leakage when used in an absorbent article or water blocking material and the like. From the same viewpoint, the water-absorption rate may also be 1 second to 12 seconds, 2 seconds to 10 seconds, 2 seconds to 8 seconds or 2 seconds to 6 seconds.

The median particle size of the water-absorbent resin particle according to the present embodiment may be 100 μm to 600 μm. As a result of the median particle size being within this range, handling ease of the water-absorbent resin particle during production of an absorbent material can be particularly favorably maintained and the thickness of the absorbent material can be reduced. From the same viewpoint, the median particle size may also be 110 μm to 500 μm, 120 μm to 500 μm, 120 μm to 400 μm, 140 μm to 400 μm, 140 μm to 350 μm or 150 μm to 350 μm.

The residual volatile component content of the water-absorbent resin particle according to the present embodiment may be 1.5% by weight or less. As a result of making the residual volatile component content to be within this range, or in other words, as a result of the water-absorbent resin particle having a low residual volatile component content, the comfort of a wearer of an absorbent article, for example, can be improved by particularly effectively inhibiting the generation of a foul odor when the water-absorbent resin particle has absorbed water. From the same viewpoint, the residual volatile component content may also be 1.3% by weight or less, 1.2% by weight or less, 0.001% by weight to 1.2% by weight, 0.001% by weight to 1.0% by weight, 0.01% by weight to 1.0% by weight, 0.01% by weight to 0.8% by weight, 0.01% by weight to 0.6% by weight or 0.01% by weight to 0.45% by weight.

Although there are no particular limitations on the specific surface area of the water-absorbent resin particle according to the present embodiment, from the viewpoint of improving the water-absorption rate, it may be 0.08 $m^2/g$ or more, 0.1 $m^2/g$ to 2.0 $m^2/g$, 0.12 $m^2/g$ to 1.0 $m^2/g$ or 0.14 $m^2/g$ to 0.5 $m^2/g$.

Although there are no particular limitations on the water-absorption capacity of physiological saline of the water-absorbent resin particle according to the present embodiment, from the viewpoint of improving the absorption volume of an absorbent article, it may be 30 g/g to 90 g/g, 35 g/g to 80 g/g, 45 g/g to 75 g/g, 50 g/g to 70 g/g or 55 g/g to 65 g/g.

The equilibrium swelling capacity (10 minute value) of the water-absorbent resin particle (which may be simply referred to as the equilibrium swelling capacity) may be 20 mm or more. As a result of the water-absorbent resin particle having high swelling capacity in this manner, when the water-absorbent resin particle is used in a water blocking material for cable, it is able to demonstrate a suitable swelling pressure to a degree that maintains water penetration preventive effects for a long period of time while not promoting deterioration of the base material of the cable after having prevented initial permeation of water caused by cracks in the cable. From the same viewpoint, the equilibrium swelling capacity may also be 21 mm to 40 mm, 22 mm to 35 mm or 23 mm to 30 mm.

The ratio of the initial swelling capacity (1 minute value) to the equilibrium swelling capacity (initial swelling ratio) of the water-absorbent resin particle may be 60% to 100%. As a result of the water-absorbent resin particle having a high initial swelling ratio in this manner, when the water-absorbent resin particle is used in a water blocking material for cable, initial permeation of water caused by cracks in the cable can be more reliably prevented. From the same viewpoint, the initial swelling ratio may be 75% to 98% or 90% to 95%.

The previously explained water-absorption rate of physiological saline, median particle size, residual volatile component content, specific surface area, water-absorption capacity of physiological saline, equilibrium swelling capacity and initial swelling ratio are all values that are measured according to the methods to be subsequently described in the examples.

There are no particular limitations on the raw materials of the water-absorbent resin particle according to the present embodiment. For example, the resin used to compose the water-absorbent resin particle can be selected so that the water-absorption rate of physiological saline, median particle size and residual volatile component content are within the numerical ranges previously described. For example, a resin obtained by polymerizing a water-soluble ethylenically unsaturated monomer (a polymer containing a water-soluble ethylenically unsaturated monomer as a monomer unit) can be used. Examples of resins obtained by polymerizing a water-soluble ethylenically unsaturated monomer include a hydrolyzed starch-acrylonitrile graft copolymer, a neutralized starch-acrylic acid graft copolymer, a saponified vinyl acetate-acrylic acid ester, and partially neutralized polyacrylic acid. Examples of methods used to polymerize the water-soluble ethylenically unsaturated monomer include aqueous polymerization and reversed-phase suspension polymerization carried out in a hydrocarbon dispersion medium and in the presence of a surfactant. The water-absorbent resin particle may contain as a main ingredient thereof a polymer containing a water-soluble ethylenically unsaturated monomer as a monomer unit. For example, the ratio of the polymer may be 50 parts by weight or more relative to 100 parts by weight of the water-absorbent resin particle.

In the case of producing the water-absorbent resin particle using a hydrophilic polymeric dispersion agent to be subsequently described, the resulting water-absorbent resin particle can contain the hydrophilic polymeric dispersion agent. The content of the hydrophilic polymeric dispersion agent in the water-absorbent resin particle may be, for example, 0.001 parts by weight to 10 parts by weight, 0.005 parts by weight to 5 parts by weight, 0.01 parts by weight to 3 parts by weight or 0.01 parts by weight to 1.5 parts by weight relative to 100 parts by weight of the water-absorbent resin particle. These contents can be derived in the same manner as the content (used amount) of hydrophilic polymeric dispersion agent relative to 100 parts by weight of the water-soluble ethylenically unsaturated monomer as will be subsequently described in the explanation of the production method of the water-absorbent resin particle.

In the case of producing the water-absorbent resin particle using a water-soluble thickener to be subsequently described, the resulting water-absorbent resin particle can contain the water-soluble thickener. The content of the water-soluble thickener in the water-absorbent resin particle may be, for example, 0.05 parts by weight to 20 parts by weight, 0.2 parts by weight to 10 parts by weight, 0.4 parts by weight to 5 parts by weight or 0.6 parts by weight to 3 parts by weight relative to 100 parts by weight of the water-absorbent resin particle (polymer solid fraction). The content of the water-soluble thickener is derived in the same manner as the content (used amount) of water-soluble thickener relative to 100 parts by weight of the water-soluble ethylenically unsaturated monomer to be subsequently described in the explanation of the production method of the water-absorbent resin particle.

The water-soluble resin particle may also contain an additive such as a heat resistance stabilizer, antioxidant or antibacterial agent corresponding to the purpose of use. Although varying according to the application of the water-absorbent resin particle, the type of additive and the like, the amounts of these additives may be 0.001 parts by weight to 10 parts by weight, 0.01 parts by weight to 5 parts by weight or 0.1 parts by weight to 2 parts by weight relative to 100 parts by weight of the water-absorbent resin particle (polymer solid fraction).

The following provides an explanation of one example of a reversed-phase suspension polymerization method. The water-absorbent resin particle according to the present embodiment can be obtained by, for example, a method in which a water-soluble ethylenically unsaturated monomer is subjected to reversed-phase suspension polymerization using a radical polymerization initiator in a suspension containing an oily liquid containing a surfactant, a hydrocarbon dispersion medium and, as necessary, a hydrophobic polymeric dispersion agent, and an aqueous liquid containing the water-soluble ethylenically unsaturated monomer. For example, at least one of the following Production Methods 1 to 3 can be employed for this method.

Namely, the water-absorbent resin particle can be obtained by a method in which reversed-phase suspension polymerization is carried out using a surfactant having an HLB value of 6 or higher and an aqueous liquid containing a hydrophilic polymer dispersion agent (Production Method 1), a method in which reversed-phase suspension polymerization is carried out using a surfactant having an HLB value of 6 or higher and an aqueous liquid having a viscosity at 20° C. of 20 mPa·s or more and/or containing a water-soluble thickener (Production Method 2), or a method in which a separate aqueous liquid is added to a suspension containing a water-containing gelated polymer at 45° C. or higher obtained by reversed-phase suspension polymerization using a suspension containing a surfactant having an HLB value of 6 or higher and an aqueous liquid, followed by carrying out reversed-phase suspension polymerization (Production Method 3).

In the case of reversed-phase suspension polymerization using a surfactant having an HLB value of 6 or higher, since the state of a W/O type reversed-phase suspension, which is formed by a continuous phase in the form of an oily liquid (O) and a discontinuous phase in the form of an aqueous liquid (W), can be favorably maintained, it tends to be possible to form fine surface irregularities both uniformly and in a large quantity on the surface of the water-absorbent resin particle. The degree of the surface irregularities can be represented by the specific surface area of the water-absorbent resin particle. A water-absorbent resin particle having a large quantity of surface irregularities on the surface thereof has a large specific surface area, and tends to demonstrate a high water-absorption rate. On the other hand, in the case of reversed-phase suspension polymerization using a surfactant, the interface between the aqueous liquid and the oily liquid is strongly activated. Consequently, during reversed-phase suspension polymerization, it may be because the fine hydrocarbon dispersion medium in the oily liquid is easily incorporated into the aqueous liquid, the residual volatile component content of the water-absorbent resin particle tends to increase. In this manner, although a water-absorbent resin particle having a large specific surface area tends to have a high water-absorption rate, there is also a strong tendency towards the generation of a foul odor following water absorption.

However, the water-absorbent resin particle according to the present embodiment, which not only has a high water-absorption rate but is also superior in terms of the generation of a foul odor following water absorption, can be obtained by employing at least one of the above-mentioned Production Methods 1 to 3. The following provides a detailed explanation of these production methods.

(Production Method 1)

Production Method 1 is provided with a polymerization step that comprises polymerizing a water-soluble ethylenically unsaturated monomer in a suspension containing an oily liquid containing a hydrocarbon dispersion medium and an aqueous liquid containing an aqueous solvent and the water-soluble ethylenically unsaturated monomer, the aqueous liquid being dispersed in the oily liquid. The above-mentioned polymerization is W/O type reversed-phase suspension polymerization in which polymerization is carried out by using the oily liquid (O) containing the hydrocarbon dispersion medium for the continuous phase and using the aqueous phase (W) containing water for the discontinuous phase in the form of droplets dispersed in the continuous phase.

The above-mentioned suspension contains a surfactant having an HLB value of 6 or higher. In addition, the aqueous liquid further contains a hydrophilic polymeric dispersion agent.

The HLB value of the surfactant may be 6 to 16, 7 to 16, 8 to 12 or 8.5 to 10.5. As a result of the HLB value of the surfactant being within these ranges, the state of the W/O type reversed-phase suspension becomes more favorable, and a particle tends to be obtained that has a more preferable particle size and a more superior water-absorption rate.

Examples of surfactants include nonionic surfactants such as sorbitan fatty acid esters, (poly)glycerol fatty acid esters (wherein, "(poly)" refers both to the case of the prefix "poly" being present and the case of it being absent, and to apply similarly hereinafter), sucrose fatty acid esters, polyoxyethylene sorbitan fatty acid esters, polyoxyethylene glycerol fatty acid esters, sorbitol fatty acid esters, polyoxyethylene sorbitol fatty acid esters, polyoxyethylene alkyl ethers, polyoxyethylene alkyl phenyl ethers, polyoxyethylene castor oils, polyoxyethylene hydrogenated castor oils, alkyl-aryl-formaldehyde condensation polyoxyethylene ethers, polyoxyethylene-polyoxypropylene block copolymers, polyoxyethylene polyoxypropyl alkyl ethers and polyethylene glycol fatty acid esters; and, anionic surfactants such as fatty acid salts, alkylbenzene sulfonates, alkylmethyl taurates, sulfate esters of polyoxyethylene alkyl phenyl ethers, sulfonates of polyoxyethylene alkyl ethers, phosphate esters of polyoxyethylene alkyl ethers and phosphate esters of polyoxyethylene alkyl allyl ethers. From the viewpoints of a favorable state of the W/O type reversed-phase suspension, facilitating the obtaining of a water-absorbent resin particle having a preferable particle size and industrial availability, the surfactant may be at least one kind of compound selected from the group consisting of sorbitan fatty acid esters, polyglycerol fatty acid esters and sucrose fatty acid esters, and from the viewpoint of improving the performance of the resulting water-absorbent resin particle as previously described, the surfactant may be a sorbitan fatty acid ester. One kind of each of these surfactants may be used alone or two or more kinds may be used in combination.

From the viewpoints of stabilizing the state of the W/O type reversed-phase suspension and selecting an efficient amount used that allows the obtaining of suspension stabilizing effects, the amount of surfactant used may be 0.1 parts by weight to 5 parts by weight, 0.2 parts by weight to 3 parts by weight or 0.4 parts by weight to 2 parts by weight relative to 100 parts by weight of the aqueous liquid. Normally, the ratio of each component can be calculated by assuming the total weight of the aqueous solvent, the water-soluble ethylenically unsaturated monomer, the hydrophilic polymeric dispersion agent and the water-soluble thickener to be subsequently described to be equal to the weight of the aqueous liquid. However, this does not mean that the hydrophilic polymeric dispersion agent and the water-soluble thickener are always essential components of the aqueous liquid.

The aqueous liquid in the Production Method 1 contains the aqueous solvent containing water, the water-soluble ethylenically unsaturated monomer, the hydrophilic polymeric dispersion agent, and depending on the case, various types of additives. The aqueous solvent is mainly composed of water and may also contain other hydrophilic solvents.

The hydrophilic polymeric dispersion agent is, for example, a polymeric dispersion agent in which the amount thereof that dissolves in 100 g of water at 25° C. may be 0.001 g to 200 g, 0.05 g to 150 g or 0.1 g to 100 g.

The hydrophilic dispersion agent may be at least one type of polymeric compound selected from the group consisting of, for example, polyvinyl alcohol (PVA), polyvinylpyrrolidone (PVP), polyethylene glycol (PEG), polypropylene glycol, polyethylene glycol-polypropylene glycol block copolymer, polyglycerol, polyoxyethylene glycerin, polyoxypropylene glycerin, polyoxyethylene-polyoxypropylene glycerin copolymer and polyoxyethylene sorbitan fatty acid ester. Among these, the hydrophilic polymeric dispersion agent may be at least one type of compound selected from the group consisting of polyvinyl alcohol, polyvinylpyrrolidone, polyethylene glycol, polypropylene glycol and polyglycerol, and from the viewpoint of the effect of reducing residual volatile component content, may be polyvinylpyrrolidone or polyvinyl alcohol. One type of each of these hydrophilic polymeric dispersion agents may be used alone or two or more types may be used in combination.

Although the polyvinylpyrrolidone, polyvinyl alcohol and the like listed as examples of the hydrophilic polymeric dispersion are also typically used as thickeners, in the present embodiment, it was unexpectedly found that residual volatile component content is reduced even if these are contained in a small amount that does not cause hardly any increase in viscosity of the aqueous liquid.

Although the mechanism by which the residual volatile component content decreases as a result of the aqueous liquid provided for reversed-phase suspension polymerization containing a hydrophilic polymeric dispersion agent is not clear, one possible reason is that the hydrophilic polymeric dispersion agent stabilizes separation and unification of droplets of the aqueous liquid in a W/O type reversed-phase suspension. More specifically, it is presumed that since the hydrophilic polymeric dispersion agent efficiently protects the vicinity of the internal surface of the aqueous liquid droplets, the frequency at which the hydrocarbon dispersion medium is incorporated in the aqueous liquid droplets during collisions between aqueous liquid droplets is decreased, thereby inhibiting the formation of O/W/O type structures.

Although the amount of the hydrophilic polymeric dispersion agent used cannot be uniformly determined since the preferable amount thereof varies according to the type and molecular weight thereof, the amount may be, for example, 0.001 parts by weight to 10 parts by weight, 0.005 parts by weight to 5 parts by weight, 0.01 parts by weight to 3 parts by weight or 0.01 parts by weight to 1.5 parts by weight relative to 100 parts by weight of the water-soluble ethylenically unsaturated monomer. In the case the amount of the hydrophilic polymeric dispersion agent used is 0.001 parts by weight or more, the effect of reducing the residual volatile component content is obtained to a higher degree, while in the case the amount is 10 parts by weight or less, effects tend to be obtained that correspond to the amount used, thereby making this more economical.

The molecular weight and the like of the hydrophilic polymeric dispersion agent is not particularly limited, and is within a range that enables the hydrophilic polymeric dispersion agent to demonstrate affinity for the aqueous solvent (and particularly, water) and uniformly disperse in the aqueous liquid. The weight average molecular weight of the hydrophilic polymeric dispersion agent may be 2,000 to 5,000,000, 5,000 to 3,000,000, 10,000 to 2,000,000, 20,000 to 1,500,000 or 30,000 to 1,500,000. As a result of making the molecular weight of the hydrophilic polymeric dispersion agent to be within these ranges, there is a tendency to achieve a suitable particle size while being able to particularly remarkably enhance the effect of reducing the residual volatile component content. The above-mentioned weight average molecular weight is a value measured by gel permeation chromatography (GPC) that is converted by using polyethylene oxide as a standard. There are no particular limitations on the degree of saponification and the like in the case the hydrophilic polymeric dispersion agent is polyvinyl alcohol. From the viewpoint of solubility in water and the effect of reducing the residual volatile component content, the degree of saponification of the polyvinyl alcohol may be 65% to 100%, 75% to 98%, 80% to 95% or 85% to 90%.

Examples of the above-mentioned water-soluble ethylenically unsaturated monomer include ethylenically unsaturated monomers containing at least one functional group selected from the group consisting of a carboxyl group, sulfo group, amido group and amino group. The water-soluble ethylenically unsaturated monomer may be at least one type selected from the group consisting of, for example, (meth)acrylic acid ("(meth)acrylic" is hereinafter used to represent both "acrylic" and "methacrylic" collectively) and salts thereof, 2-(meth)acrylamido-2-methylpropanesulfonic acid and salts thereof, (meth)acrylamide, N,N-dimethyl(meth)acrylamide, 2-hydroxyethyl(meth)acrylate, N-methylol(meth)acrylamide, polyethylene glycol mono(meth)acrylate, N,N-diethylaminoethyl(meth)acrylate, N,N-diethylaminopropyl(meth)acrylate and diethylaminopropyl(meth)acrylamide. In the case the water-soluble ethylenically unsaturated monomer contains an amino group, the amino group may be quaternized. Functional groups such as a carboxyl group or amino group possessed by the monomer function as crosslinkable functional groups in a post-crosslinking step to be subsequently described. One type of these water-soluble ethylenically unsaturated monomers may be used alone or two or more types may be used in combination.

From the viewpoint of industrial availability, the water-soluble ethylenically unsaturated monomer may be at least one type of compound selected from the group consisting of acrylic acid and salts thereof, methacrylic acid and salts thereof, acrylamide, methacrylamide and N,N-dimethylacrylamide, may be at least one type of compound selected from the group consisting of acrylic acid and salts thereof, methacrylic acid and salts thereof and acrylamide, and from the viewpoint of further enhancing safety, may be at least one type of compound selected from the group consisting of acrylic acid and salts thereof and methacrylic acid and salts thereof.

The concentration of the water-soluble ethylenically unsaturated monomer in the aqueous liquid may be within the range of 20% by weight to the saturated concentration based on the aqueous liquid (total weight of the aqueous solvent, water-soluble ethylenically unsaturated monomer, hydrophilic polymeric dispersion agent and a water-soluble thickener to be subsequently described). In addition, from the viewpoints of facilitating the obtaining of a water-absorbent resin particle having a preferable particle size due to a favorable state of the W/O type reversed-phase suspension, and improving the swelling capacity of the resulting water-absorbent resin particle, the above-mentioned concentration may be 25% by weight to 50% by weight, 30% by weight to 45% by weight or 35% by weight to 42% by weight.

In the case the water-soluble ethylenically unsaturated monomer has an acid radical in the manner of (meth)acrylic acid or 2-(meth)acrylamido-2-methylpropanesulfonic acid, the acid group may be neutralized by an alkaline neutralizing agent such as an alkaline metal salt to form a salt. Examples of alkaline neutralizing agents include aqueous solutions of sodium hydroxide, potassium hydroxide and ammonia. One type each of these alkaline neutralizing agents may be used alone or two or more types may be used in combination.

From the viewpoints of enhancing swelling capacity by increasing the osmotic pressure of the resulting water-absorbent resin particle and further preventing problems relating to safety and the like by inhibiting the residual presence of excess alkaline neutralizing agent, the neutralization degree of the alkaline neutralizing agent on all acid groups may be 10 mol % to 100 mol %, 30 mol % to 90 mol %, 50 mol % to 80 mol % or 60 mol % to 78 mol %.

The above-mentioned aqueous liquid may contain a radial polymerization initiator. In this case, the radical polymerization initiator may be water-soluble. Examples of radial polymerization initiators include persulfates such as potassium persulfate, ammonium persulfate and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate and hydrogen peroxide; and, azo compounds such as 2,2'-azobis(2-methylpropionamidine)dihydrochloride, 2,2'-azobis[2-(N-phenylamidino)propane]dihydrochloride, 2,2'-azobis[2-(N-allylamidino)propane]dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide] and 4,4'-azobis(4-cyanovaleric acid). One type of each of these radical polymerization initiators may be used alone or two or more types may be used in combination.

The amount of the radical polymerization initiator used may be normally 0.005 mol to 1 mol relative to 100 mol of the water-soluble ethylenically unsaturated monomer. If the amount of the radical polymerization initiator used is 0.005 mol or more, the polymerization reaction does not require a long period of time, thereby making this efficient. If the amount used is 1 mol or less, the polymerization reaction tends to not occur rapidly.

The radical polymerization initiator can also be used as a redox polymerization initiator by using in combination with a reducing agent such as sodium sulfite, sodium bisulfite, ferrous sulfate or L-ascorbic acid.

The aqueous liquid may contain a chain transfer agent to control water absorption performance of the water-absorbent resin particle. Examples of chain transfer agents include hypophosphites, thiols, thiolic acids, secondary alcohols and amines.

The oily liquid is a hydrophobic liquid mainly composed of a hydrocarbon dispersion medium. The hydrocarbon dispersion medium can be used as a dispersion medium of the aqueous liquid during reversed-phase suspension polymerization.

Examples of the hydrocarbon dispersion medium include chain aliphatic hydrocarbons such as n-hexane, n-heptane, 2-methylhexane, 3-methylhexane, 2,3-dimethylpentane, 3-ethylpentane and n-octane; alicyclic hydrocarbons such as cyclohexane, methylcyclohexane, cyclopentane, methylcyclopentane, trans-1,2-dimethylcyclopentane, cis-1,3-dimethylcyclopentane and trans-1,3-dimethylcyclopentane; and, aromatic hydrocarbons such as benzene, toluene and xylene. One type each of these hydrocarbon dispersion media may be used alone or two or more types may be used in combination. The hydrocarbon dispersion medium may be at least one type of compound selected from the group consisting of chain aliphatic hydrocarbons having 6 to 8 carbon atoms and alicyclic hydrocarbons having 6 to 8 carbon atoms. From the viewpoints of a favorable state of the W/O type reversed-phase suspension, facilitating the obtaining of a water-absorbent resin particle having a superior water-absorption rate and preferable particle size, industrial availability and stable quality, the hydrocarbon dispersion medium may be n-heptane or cyclohexane. In addition, from the same viewpoints, a mixture of the hydrocarbon dispersion media may be, for example, commercially available Exxsol Heptane (ExxonMobil, containing 75% to 85% of n-heptane and isomeric hydrocarbons).

From the viewpoints of removing excessive heat of polymerization and facilitating control of polymerization temperature, the amount of the hydrocarbon dispersion medium contained in the oily liquid may be 50 parts by weight to 650 parts by weight, 70 parts by weight to 550 parts by weight or 100 parts by weight to 450 parts by weight relative to 100 parts by weight of the water-soluble ethylenically unsaturated monomer. As a result of making the amount of the hydrocarbon dispersion medium used be 50 parts by weight or more, it tends to be easy to control the polymerization temperature. By making the amount of the hydrocarbon dispersion medium used to be 650 parts by weight or less, polymerization productivity tends to improve, thereby making this economical.

The oily liquid may also contain a hydrophobic polymeric dispersion agent. Combining the use of a surfactant and a hydrophobic polymeric dispersion agent makes it possible to further stabilize the state of the W/O type reversed-phase suspension. Examples of hydrophobic polymeric dispersion agents include maleic anhydride-modified polyethylene, maleic anhydride-modified polypropylene, maleic anhydride-modified ethylene-propylene copolymer, maleic anhydride-modified EPDM (ethylene-propylene-diene terpolymer), maleic anhydride-modified polybutadiene, ethylene-maleic anhydride copolymer, ethylene-propylene-maleic anhydride copolymer, butadiene-maleic anhydride copolymer, oxidized polyethylene, ethylene-acrylic acid copolymer, ethyl cellulose, ethyl hydroxyethyl cellulose and the like. Among these, maleic anhydride-modified polyethylene, maleic anhydride-modified polypropylene, maleic anhydride-modified ethylene-propylene copolymer, oxidized polyethylene or ethylene-acrylic acid copolymer can be used in terms of stability of the W/O type reversed-phase suspension. One type each of these hydrophobic polymeric dispersion agents may be used alone or two or more types may be used in combination.

The amount of hydrophobic polymeric dispersion agent contained in the oily liquid may be 0.1 parts by weight to 5 parts by weight, 0.2 parts by weight to 3 parts by weight or 0.4 parts by weight to 2 parts by weight relative to 100 parts by weight of the aqueous liquid (total weight of the aqueous solvent, water-soluble ethylenically unsaturated monomer, hydrophilic polymeric dispersion agent and water-soluble thickener).

The oily liquid and the aqueous liquid are normally each prepared prior to polymerization in the case of reversed-phase suspension polymerization. The suspension used for polymerization is prepared by mixing the prepared aqueous liquid and oily liquid.

There are no particular limitations on the method used to incorporate the hydrophilic polymeric dispersion agent provided it can be uniformly dispersed in the aqueous liquid prior to polymerization, and examples of such methods include: (a) mixing the hydrophilic polymeric dispersion agent into a water-soluble ethylenically unsaturated monomer solution and dissolving to obtain an aqueous liquid, followed by dispersing this in the oily liquid, (b) separately adding a water-soluble ethylenically unsaturated monomer solution and an aqueous solution of the hydrophilic polymeric dispersion agent to the oily liquid and dispersing therein, and (c) dispersing an water-soluble ethylenically unsaturated monomer solution in the oily liquid followed by adding an aqueous solution of the hydrophilic polymeric dispersion agent and dispersing therein prior to polymerization. Among these, the method of (a) can be used from the viewpoint of more effectively reducing the residual volatile component content.

A surfactant can be added to the oily liquid.

The polymerization temperature when carrying out reversed-phase suspension polymerization (temperature of the suspension) cannot be uniformly determined since it varies according to the type of radical polymerization initiator used. Normally, from the viewpoints of shortening polymerization time by allowing polymerization to proceed rapidly, facilitating removal of heat of polymerization and carrying out the reaction smoothly, the polymerization temperature may be 20° C. to 110° C. or 40° C. to 90° C. The reaction time is normally 0.5 hours to 4 hours.

As was previously described, a particulate water-containing gelated polymer is formed by polymerizing the water-soluble ethylenically unsaturated monomer. Normally, the resulting polymer (water-containing gelated polymer) has various forms such as spherical, granular, fragmented, confetti-shaped or an agglomerate thereof. In the present embodiment, from the viewpoints of improving specific surface area and water-absorption rate, the water-containing gelated polymer may be granular or may be granular and having numerous protrusions on the surface thereof.

Production Method 1 may be further provided with a post-crosslinking step for crosslinking the above-mentioned water-containing gelated polymer. Production Method 1 may also be provided with a primary drying step prior to the post-crosslinking step for adjusting the weight percentage of water in the water-containing gelated polymer (water content of the water-containing gelated polymer) so as to be, for example, 20% by weight to 130% by weight based on a value of 100% by weight for components derived from the water-soluble ethylenically unsaturated monomer (polymer solid fraction) that composes the water-containing gelated polymer.

Although there are no particular limitations on the drying method of the primary drying step, examples thereof include: (a) a method in which water is removed by azeotropic distillation of heating the water-containing gelated polymer from the outside while the water-containing gelated polymer dispersed in the oily liquid (hydrocarbon dispersion medium) and the hydrocarbon dispersion medium refluxed, (b) a method in which the water-containing gelated polymer is removed by decantation and dried under reduced pressure, and (c) a method in which the water-containing gelated polymer is filtered out with a filter and dried under reduced pressure. In particular, the method of (a) can be employed in consideration of simplicity of the production process.

A water-absorbent resin particle having more superior water-absorption performance can be obtained by crosslinking a water-containing gelated polymer in which the water content of the water-containing gelated polymer has been adjusted to, for example, 20% by weight to 130% by weight in the manner described above.

Post-crosslinking of the water-containing gelated polymer is carried out by, for example, mixing the water-containing gelated polymer with a post-crosslinking agent followed by heating. The post-crosslinking agent may be a water-soluble compound having a functional group capable of reacting with a functional group contained in the water-soluble ethylenically unsaturated monomer (such as a carboxyl group in the case of acrylic acid). Examples of post-crosslinking agents include polyols such as ethylene glycol, propylene glycol, 1,4-butanediol, trimethylolpropane, glycerin, polyoxyethylene glycol, polyoxypropylene glycol and polyglycerol; compounds having two or more epoxy groups such as (poly)ethylene glycol diglycidyl ether, (poly)propylene glycol diglycidyl ether and (poly)glycerol diglycidyl ether; haloepoxy compounds such as epichlorohydrin, epibromohydrin and $\alpha$-methylepichlorohydrin; compounds having two and more isocyanate groups such as 2,4-tolylene diisocyanate or hexamethylene diisocyanate; oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol and 3-butyl-3-oxetaneethanol; oxazoline compounds such as 1,2-ethylenebisoxazoline; carbonate compounds such as ethylene carbonate; and, hydroxyalkylamide compounds such as bis[N,N-di($\beta$-hydroxyethyl)] adipamide. The post-crosslinking agent may be a compound that has two or more functional groups within a molecule thereof that are capable of reacting with a functional group possessed by the water-soluble ethylenically unsaturated monomer. Examples of such compounds include polyols, compounds having two or more epoxy groups, haloepoxy compounds and compounds having two or more isocyanate groups as mentioned above. One type each of these post-crosslinking agents may be used alone or two or more types may be used in combination.

From the viewpoint of superior reactivity, the post-crosslinking agent may be a compound having two or more epoxy groups. From the viewpoints of high solubility in water and handling ease as a post-crosslinking agent in particular, the post-crosslinking agent may be at least one type of compound selected from the group consisting of ethylene glycol diglycidyl ether, propylene glycol diglycidyl ether, glycerol diglycidyl ether, polyethylene glycol diglycidyl ether and polyglycerol glycidyl ether, and from the viewpoint of improving various performance of the resulting water-absorbent resin particle as previously described, may be ethylene glycol diglycidyl ether or propylene glycol diglycidyl ether.

The amount of the post-crosslinking agent may be 0.0001 mol to 1 mol, 0.0005 mol to 0.5 mol, 0.001 mol to 0.1 mol or 0.005 mol to 0.05 mol relative to 100 mol of the water-soluble ethylenically unsaturated monomer used to form the water-containing gelated polymer. If the amount of the post-crosslinking agent is 0.0001 mol or more, there is a tendency that the effects of crosslinking are demonstrated, and the water-absorption rate of the water-absorbent resin particle can be further improved without causing the surface of the water-absorbent resin particle to become viscous during water absorption. If the amount of the post-crosslinking agent is 1 mol or less, water-absorption capacity of the water-absorbent resin particle tends to be able to be further improved without causing excessive crosslinking.

Mixing of the water-containing gelated polymer and the post-crosslinking agent can be carried out after having adjusted the water content of the water-containing gelated polymer to be within a specific range with the primary drying step and the like. The post-crosslinking reaction is able to proceed more preferably by controlling the water content of the water-containing gelated polymer during mixing of the water-containing gelated polymer and the post-crosslinking agent in this manner.

The water content of the water-containing gelated polymer provided for the post-crosslinking step may be 20% by weight to 130% by weight, 25% by weight to 110% by weight, 30% by weight to 90% by weight, 35% by weight to 80% by weight or 40% by weight to 70% by weight. As a result of making the water content of the water-containing gelated polymer to be within these ranges, production efficiency can be enhanced by shortening the primary drying step while further improving water-absorption performance with the post-crosslinking reaction.

The water content of the water-containing gelated polymer can be determined by calculating the value obtained by adding the amount of water used as necessary when mixing the post-crosslinking agent to the value obtained by subtracting the amount of water extracted to the outside by the primary drying step from the amount of water contained in the aqueous liquid prior to polymerization (the amount of water of the primary dried gel), as the amount of water of the water-containing gelated polymer, followed by calculating the ratio of the above-mentioned amount of water of the water-containing gelated polymer to the weight of the water-soluble ethylenically unsaturated monomer that composes the water-containing gelated polymer.

The weight of components derived from the water-soluble ethylenically unsaturated monomer that composes the water-containing gelated polymer is determined by calculating as the theoretical polymer solid fraction from the total weight of the water-soluble ethylenically unsaturated monomer used in the polymerization reaction.

When mixing the water-containing gelated polymer and the post-crosslinking agent, water may be added as a solvent that dissolves the post-crosslinking agent in order to uniformly disperse the post-crosslinking agent. From the viewpoint of uniformly dispersing the post-crosslinking agent while enhancing process economy by rationally shortening the drying step, the weight ratio of the amount of water of the primary dried gel (water-containing gelated polymer) and the amount of water added together with the post-crosslinking agent may be 100:0 to 60:40, 99:1 to 70:30, 98:2 to 80:20 or 98:2 to 90:10. A hydrophilic organic solvent may be used instead of or in combination with water. Examples of hydrophilic organic solvents include lower alcohols such as methyl alcohol, ethyl alcohol and isopropyl alcohol; ketones such as acetone and methyl ethyl ketone; ethers such as dioxane and tetrahydrofuran; amides such as N,N-dimethylformamide; and, sulfoxides such as dimethylsulfoxide. One type of each of these solvents may be used alone or two or more types may be used in combination as necessary.

The reaction temperature of the post-crosslinking reaction may be 60° C. or higher, 70° C. to 200° C. or 80° C. to 150° C. As a result of making the reaction temperature to be 60° C. or higher, the post-crosslinking reaction is accelerated and the reaction tends to not require an excessive amount of time. As a result of making the reaction temperature to be 200° C. or lower, deterioration of the resulting water-absorbent resin particle and a decrease in water-absorption performance tend to be able to be inhibited.

Although the reaction time of the post-crosslinking reaction cannot be uniformly determined since it varies according to the reaction temperature, type and amount of the post-crosslinking agent and the like, it may be, for example, 1 minute to 300 minutes or 5 minutes to 200 minutes.

Production Method 1 may also be provided with a secondary drying step for further removing water, the hydrocarbon dispersion medium and the like by distillation of applying energy such as heat from the outside after having carried out the post-crosslinking reaction. Carrying out this secondary drying step tends to allow the obtaining of a water-absorbent resin particle having more superior fluidity.

There are no particular limitations on the method of the secondary drying step, and examples thereof include: (a) a method in which water, hydrocarbon dispersion medium and the like are simultaneously removed by distilling a mixture of resin particles dispersed in the oily liquid (hydrocarbon dispersion medium) after the post-crosslinking reaction, (b) a method in which resin particles are removed by decantation and then dried under reduced pressure, and (c) a method in which resin particles are filtered out with a filter and dried under reduced pressure. Among these, the method of (a) can be employed in consideration of simplicity of the production process.

According to Production Method 1, a water-absorbent resin particle according to the present embodiment described above can be obtained. The resulting water-absorbent resin particle has a particle size of a suitable size, a superior water-absorption rate, and a low residual volatile component content.

(Production Method 2)

Production Method 2 is provided with a polymerization step that comprises polymerizing a water-soluble ethylenically unsaturated monomer in a suspension containing an oily liquid containing a hydrocarbon dispersion medium and an aqueous liquid containing an aqueous solvent and the water-soluble ethylenically unsaturated monomer, the aqueous liquid being dispersed in the oily liquid. The above-mentioned polymerization is W/O type reversed-phase suspension polymerization in which polymerization is carried out by using the oily liquid (O) containing the hydrocarbon dispersion medium for the continuous phase and using the aqueous phase (W) containing water for the discontinuous phase in the form of droplets dispersed in the continuous phase. The aqueous liquid has a viscosity of 20 mPa·s or more at 20° C.

The above-mentioned suspension further contains a surfactant having an HLB value of 6 or higher.

The amount of surfactant used can be adjusted within the same range as that of Production Example 1. In the case of not using a hydrophilic polymeric dispersion agent, the amount of the surfactant used can normally be set by considering the total weight of the aqueous solvent, water-soluble ethylenically unsaturated monomer and, depending on the case, a water-soluble thickener, to be equal to the weight of the aqueous liquid.

In Production Method 2, the aqueous liquid contains an aqueous solvent containing water, the water-soluble ethylenically unsaturated monomer and, depending on the case, various types of additives such as a water-soluble thickener. The aqueous solvent is composed mainly of water and may also contain other hydrophilic solvents.

The viscosity of the aqueous liquid in Production Method 2 at 20° C. is 20 mPa·s or more. This viscosity may also be 20 mPa·s to 500,000 mPa·s, 25 mPa·s to 500,000 mPa·s, 25 mPa·s to 200,000 mPa·s, 30 mPa·s to 200,000 mPa·s, 30 mPa·s to 100,000 mPa·s, 35 mPa·s to 100,000 mPa·s, 35 mPa·s to 50,000 mPa·s, 40 mPa·s to 50,000 mPa·s or 40 mPa·s to 10,000 mPa·s. The residual volatile component content can be particularly remarkably reduced by making this viscosity to be 20 mPa·s or more. In addition, transfer of the aqueous liquid tends to be made easier by making this viscosity to be 500,000 mPa·s or less. The above-mentioned viscosity of the aqueous liquid is a value obtained when measuring at 20° C. and 60 rpm with a Brookfield rotational viscometer (LVDV-1).

The aqueous liquid may contain a water-soluble thickener for the purpose of obtaining an aqueous liquid having the viscosity described above. The amount of this water-soluble thickener that dissolves in 100 g of water at 25° C. may be 1 g to 300 g, 3 g to 250 g or 5 g to 200 g. Examples of water-soluble thickeners include hydroxyalkyl celluloses such as hydroxyethyl cellulose (HEC) and hydroxypropyl cellulose (HPC); hydroxyalkyl alkyl celluloses such as hydroxyethyl methyl cellulose, hydroxypropyl methyl cellulose and hydroxyethyl ethyl cellulose; carboxyalkyl celluloses such as carboxymethyl cellulose; and, carboxyalkyl hydroxyalky celluloses such as carboxymethyl hydroxyethyl cellulose. Among these, the water-soluble thickener may be at least one type of compound selected from the group consisting of hydroxyalkyl celluloses, hydroxyalkyl alkyl celluloses and carboxyalkyl hydroxyalkyl celluloses, and may also be hydroxyethyl cellulose and hydroxypropyl cellulose. Hydroxyethyl cellulose and hydroxypropyl cellulose are highly soluble in aqueous solutions, more easily realize the effect of increasing viscosity of an aqueous solution, and are able to further reduce the residual volatile component content of the water-absorbent resin particle. One type each of these water-soluble thickeners may be used alone or two or more types may be used in combination.

Although there are no particular limitations on the amount of the water-soluble thickener in the case the aqueous liquid contains a water-soluble thickener, it may be, for example 0.05 parts by weight to 20 parts by weight, 0.2 parts by weight to 10 parts by weight, 0.4 parts by weight to 5 parts by weight or 0.6 parts by weight to 3 parts by weight relative to 100 parts by weight of the water-soluble ethylenically unsaturated monomer. The effect of increasing viscosity tends to be able to be obtained to a higher degree in the case the amount of water-soluble thickener in the aqueous liquid is 0.05 parts by weight or more. Effects corresponding to the amount tend to be able to be obtained in the case the amount of water-soluble thickener is 20 parts by weight or less, thereby making this economical.

Although the mechanism by which the residual volatile component content decreases as a result of the viscosity of the aqueous liquid at 20° C. being 20 mPa·s or more or 20 mPa·s to 500,000 mPa·s is not clear, one possible reason is that separation and unification of aqueous liquid droplets in the W/O type reversed-phase suspension are stabilized. More specifically, it is presumed that, as a result of imparting a certain viscosity or higher to aqueous liquid droplets by using a water-soluble thickener and the like, the frequency at which the hydrocarbon dispersion medium is incorporated in the aqueous liquid droplets during collisions between aqueous liquid droplets is decreased, thereby inhibiting the formation of O/W/O type structures.

Although the mechanism by which the residual volatile component content decreases as a result of the aqueous liquid containing a water-soluble thickener is not clear, this may be due to the viscosity of the aqueous liquid reaching a certain level or higher, thereby stabilizing the separation and unification of aqueous liquid droplets in the W/O type reversed-phase suspension. More specifically, it is presumed that, as a result of imparting a certain viscosity or higher to the aqueous liquid droplets by using a water-soluble thickener, the frequency at which the hydrocarbon dispersion medium is incorporated in the aqueous liquid droplets during collisions between aqueous liquid droplets is decreased, thereby inhibiting the formation of 0/W/0 type structures.

The concentration of the water-soluble ethylenically unsaturated monomer in the aqueous liquid can be adjusted within the same range as that of Production Method 1 based on the weight of the aqueous liquid (for example, the total weight of the aqueous solvent, the water-soluble ethylenically unsaturated monomer, the hydrophilic polymeric dispersion agent, and the water-soluble thickener). In the case of not using a hydrophilic polymeric dispersion agent, the concentration of the water-soluble ethylenically unsaturated monomer can be set by considering the total weight of the aqueous solvent, the water-soluble ethylenically unsaturated monomer and, depending on the case, the water-soluble thickener to be equal to the weight of the aqueous liquid.

In Production Method 2, the same types of compounds as those previously described in Production Method 1 can be used in amounts within the same ranges for the aqueous solvent, water-soluble ethylenically unsaturated monomer and radical polymerization initiator contained in the aqueous liquid, the hydrocarbon dispersion medium contained in the oily liquid, as well as the surfactant and various other additives. In addition, polymerization, post-crosslinking, drying and the like can be carried out in Production Method 2 using the same methods as Production Method 1.

According to Production Method 2, a water-absorbent resin particle according to the present embodiment described above can be obtained. The water-absorbent resin particle has a particle size of a suitable size, a superior water-absorption rate, and a low residual volatile component content.

(Production Method 3)

Production Method 3 is provided with a first polymerization step and a second polymerization step as described below. In the first polymerization step, a suspension containing a water-containing gelated polymer is obtained by polymerizing a water-soluble ethylenically unsaturated monomer in a suspension which contains an oily liquid containing a hydrocarbon dispersion medium and a surfactant having an HLB value of 6 or higher, and a first aqueous liquid containing an aqueous solvent, the water-soluble ethylenically unsaturated monomer and a radical polymerization initiator, and in which the first aqueous liquid in the form of droplets is dispersed in the oily liquid. In the second polymerization step, a suspension containing the water-containing gelated polymer at 45° C. or higher is mixed with a second aqueous liquid containing an aqueous solvent, a water-soluble ethylenically unsaturated monomer and a radical polymerization initiator, and polymerizing the water-soluble ethylenically unsaturated monomer in a suspension in which the second aqueous liquid in the form of droplets is dispersed. The polymerization in the first polymerization step and the second polymerization step is W/O type reversed-phase suspension polymerization in which polymerization is carried out by using the oily liquid (O) containing the hydrocarbon dispersion medium for the continuous phase and using the aqueous phase (W) containing water for the discontinuous phase.

The first aqueous liquid contains an aqueous solvent containing water, a water-soluble ethylenically unsaturated monomer, a radical polymerization initiator, and depending on the case, various types of additives. The aqueous solvent is mainly composed of water and may also contain other hydrophilic solvents.

The concentration of the water-soluble ethylenically unsaturated monomer in the first aqueous liquid may be within the range of, for example, 20% by weight to the saturated concentration based on the weight of the first aqueous liquid (the total weight of the aqueous solvent, water-soluble ethylenically unsaturated monomer, hydrophilic polymeric dispersion agent and water-soluble thickener). From the viewpoints of facilitating the obtaining of a water-absorbent resin particle having a preferable particle size due to a favorable state of the W/O type reversed-phase suspension, and improving the swelling capacity of the resulting water-absorbent resin particle, the above-mentioned concentration may be 25% by weight to 50% by weight, 30% by weight to 45% by weight or 35% by weight to 42% by weight.

In the first polymerization step of Production Method 3, the same types of compounds as those previously described in Production Methods 1 and 2 can be used in amounts within the same ranges for the aqueous solvent, water-soluble ethylenically unsaturated monomer and radical polymerization initiator contained in the first aqueous liquid, the hydrocarbon dispersion medium contained in the oily liquid, as well as the surfactant and other arbitrary materials. For example, the first aqueous liquid may contain a hydrophilic polymeric dispersion agent, water-soluble thickener, chain transfer agent and the like in the same manner as the aqueous liquid in Production Methods 1 and 2. In addition, polymerization in the first polymerization step is carried out using the same method as the polymerization of Production Method 1.

In the first polymerization step, a particulate water-containing gelated polymer is formed by polymerizing the water-soluble ethylenically unsaturated monomer. Production Method 3 may be further provided with an intermediate crosslinking step for crosslinking the water-containing gelated polymer prior to the second polymerization step. Intermediate crosslinking of the water-containing gelated polymer is carried out by, for example, mixing the water-containing gelated polymer with an intermediate crosslinking agent followed by heating. A compound similar to the post-crosslinking agent described in Production Method 1 is used for the intermediate cross-linking agent.

The mixed amount of the intermediate crosslinking agent may be, for example, 0.0001 mol to 0.03 mol, 0.0005 mol to 0.02 mol, 0.001 mol to 0.015 mol or 0.001 mol to 0.01 mol relative to 100 mol of the water-soluble ethylenically unsaturated monomer used to form the water-containing gelated polymer. If the mixed amount of the intermediate crosslinking agent is 0.0001 mol or more, absorption of the water-soluble ethylenically unsaturated monomer in the second aqueous liquid into the water-containing gelated polymer after the intermediate crosslinking step is inhibited, and decreases in water-absorption rate and swelling capacity tend to be able to be inhibited. If the mixed amount of the intermediate crosslinking agent is 0.03 mol or less, a decrease in water absorption performance of the water-absorbent resin particle due to excessive crosslinking tends to be able to be inhibited. The reaction temperature of the intermediate crosslinking reaction may be 60° C. or higher or 70° C. to the boiling point temperature of the hydrocarbon dispersion medium during the first polymerization. Although the reaction time of the intermediate crosslinking reaction cannot be uniformly determined since it varies according to the reaction temperature, the type and mixed amount of the intermediate crosslinking agent and the like, it may be normally 1 minute to 200 minutes, 5 minutes to 100 minutes or 10 minutes to 60 minutes.

Continuing, the following provides a detailed explanation of the second polymerization step of Production Method 3. The second polymerization step may be carried out multiple times. The number of times the second polymerization step is carried out in the case it is carried out multiple times may be 2 times or more, and from the viewpoint of reducing the residual volatile component content while enhancing productivity, may be 2 times or 3 times.

The suspension containing the water-containing gelated polymer obtained following polymerization in the first polymerization step is, with cooling as necessary, adjusted to 45° C. or higher. The suspension may be adjusted to 50° C. to 100° C., 55° C. to 90° C., 60° C. to 85° C. or 65° C. to 80° C. Subsequently, the suspension containing the water-containing gelated polymer is mixed with the second aqueous liquid containing the aqueous solvent, water-soluble ethylenically unsaturated monomer and radical polymerization initiator, and the second aqueous liquid is dispersed in the form of droplets. In the second polymerization step, the temperature of the suspension containing the water-containing gelated polymer when the suspension is mixed with the entire amount of the second aqueous liquid (at the point the suspension containing the water-containing gelated polymer is finished being mixing with the entire amount of the second aqueous liquid) may be 35° C. or higher, 40° C. to 90° C., 45° C. to 85° C. or 50° C. to 80° C. As a result of making the temperature of the suspension containing the water-containing gelated polymer before and after mixing the suspension with the second aqueous liquid to within the above-mentioned range, the residual volatile component content of the resulting water-absorbent resin particle can be efficiently reduced.

The same type of compounds as those previously described in the explanation of the first aqueous liquid, for example, can be used within the same ranges for the water-soluble ethylenically unsaturated monomer and radical polymerization initiator contained in the second aqueous liquid. The first and second aqueous liquids may be composed of the same monomer and the like or they may be composed of different monomers and the like.

In the second polymerization step, the above-mentioned water-soluble ethylenically unsaturated monomer is contained in the second aqueous liquid at a ratio of, for example, 20 parts by weight to 250 parts by weight, 40 parts by weight to 200 parts by weight or 60 parts by weight to 150 parts by weight relative to 100 parts by weight of the water-soluble ethylenically unsaturated monomer contained in the first aqueous liquid. As a result of making the amount of the water-soluble ethylenically unsaturated monomer used in the second aqueous liquid to be 20 parts by weight or more, the residual volatile component content of the resulting water-absorbent resin particle tends to further decrease, and as a result of making the amount used to be 250 parts by weight or less, the particle size of the resulting water-absorbent resin particle tends to be able to be inhibited from becoming excessively large.

From the viewpoint of improving productivity, the concentration of the water-soluble ethylenically unsaturated monomer in the second aqueous liquid in the second polymerization step may be, for example, 1% by weight or more, 2% by weight to 25% by weight, 3% by weight to 20% by weight or 4% by weight to 15% by weight higher than the concentration in the first polymerization step based on the weight of the second aqueous liquid (total weight of the aqueous solvent, water-soluble ethylenically unsaturated monomer, hydrophilic polymeric dispersion agent and water-soluble thickener).

The second polymerization step can be carried out under the same conditions as the first polymerization step in the case of carrying out the second polymerization step after having mixed the suspension containing the water-containing gelated polymer obtained after the first polymerization step with the second aqueous liquid containing the aqueous solvent, water-soluble ethylenically unsaturated monomer and radical polymerization initiator. A particulate water-containing gelated polymer is further formed by polymerizing the water-soluble ethylenically unsaturated monomer as previously described. Normally, a polymer (water-containing gelated polymer) obtained in a polymerization step can be obtained in various forms such as spherical, granular, fragmented, confetti-shaped or an agglomerate thereof. In the present embodiment, from the viewpoints of improving specific surface area and water-absorption rate, the water-containing gelated polymer may be granular or may be granular and having numerous protrusions on the surface thereof.

According to Production Method 3, it is possible to improve productivity of the resulting water-absorbent resin particle by carrying reversed-phase suspension polymerization two or more times in a single process. More surprisingly, the residual volatile component content of the resulting water-absorbent resin particle can be considerably reduced. In addition, although there is normally concern over detrimental effects on the particle size and water-absorption performance of the water-absorbent resin particle if the second polymerization step is carried out with the suspension subjected to the first polymerization step, the inventors of the present invention found that, according to Production Method 3, both improvement of water-absorption performance and productivity as well as a reduction in the residual volatile component content can be realized.

Although the mechanism by which the residual volatile component content decreases as a result of carrying out the second polymerization step is not clear, it is presumed that, due to the presence of the water-containing gelated polymer obtained in the first polymerization step when carrying out the second polymerization step, separation and unification of aqueous liquid droplets in a W/O type reversed-phase suspension system is stabilized, or in other words, the frequency at which the hydrocarbon dispersion medium is incorporated in the aqueous liquid droplets during collisions between aqueous liquid droplets is decreased, thereby inhibiting the formation of 0/W/0 type structures.

Production Method 3 may also be further provided with a post-crosslinking step for crosslinking the water-containing gelated polymer obtained in the above-mentioned final (second) polymerization step. Production Method 3 may also be provided with a primary drying step prior to the post-crosslinking step for adjusting the weight percentage of water in the water-containing gelated polymer (water content of the water-containing gelated polymer) so as to be, for example, 20% by weight to 130% by weight based on a value of 100% by weight for components derived from the water-soluble ethylenically unsaturated monomer (polymer solid fraction) in the water-containing gelated polymer.

Although there are no particular limitations on the drying method of the primary drying step, examples thereof include: (a) a method in which water is removed by azeotropic distillation of heating the water-containing gelated polymer from the outside while the water-containing gelated polymer dispersed in the oily liquid (hydrocarbon dispersion medium) and the hydrocarbon dispersion medium refluxed, (b) a method in which the water-containing gelated polymer is removed by decantation and dried under reduced pressure, and (c) a method in which the water-containing gelated polymer is filtered out with a filter and dried under reduced pressure. In particular, the method of (a) can be employed in consideration of simplicity of the production process.

A water-absorbent resin particle having more superior water-absorption performance can be obtained by crosslinking a water-containing gelated polymer in which the water content of the water-containing gelated polymer has been adjusted to, for example, 20% by weight to 130% by weight in the manner described above.

Post-crosslinking of the water-containing gelated polymer is carried out, for example, by mixing the post-crosslinking agent with the water-containing gelated polymer, followed by heating. The post-crosslinking agent as that described in Production Method 1 is used for the cross-linking agent. The intermediate crosslinking agent and the post-crosslinking agent may be the same or different.

The mixed amount of the post-crosslinking agent may be 0.0001 mol to 1 mol, 0.0005 mol to 0.5 mol, 0.001 mol to 0.1 mol or 0.005 mol to 0.05 mol relative to 100 mol of the water-soluble ethylenically unsaturated monomer used to form the water-containing gelated polymer. If the mixed amount of the post-crosslinking agent is 0.0001 mol or more, there is a tendency that the effects of crosslinking are demonstrated, and the water-absorption rate of the water-absorbent resin particle can be further improved without causing the surface of the water-absorbent resin particle to become viscous during water absorption. If the mixed amount of the post-crosslinking agent is 1 mol or less, water-absorption capacity of the water-absorbent resin particle tends to be able to be further improved without causing excessive crosslinking.

Mixing of the water-containing gelated polymer and the post-crosslinking agent can be carried out after having adjusted the water content of the water-containing gelated polymer to be within a specific range (with the primary drying step). The post-crosslinking reaction is able to proceed more preferably by controlling the water content of the water-containing gelated polymer during mixing of the water-containing gelated polymer and the post-crosslinking agent.

The water content of the water-containing gelated polymer provided for the post-crosslinking step may be, for example, 20% by weight to 130% by weight, 25% by weight to 110% by weight, 30% by weight to 90% by weight, 35% by weight to 80% by weight or 40% by weight to 70% by weight. As a result of making the water content of the water-containing gelated polymer to be within these ranges, water-absorption performance can be further improved by the post-crosslinking reaction while enhancing production efficiency with shortening the primary drying step.

The water content of the water-containing gelated polymer can be determined by calculating the value obtained by adding the amount of water used as necessary when mixing the intermediate crosslinking agent or the post-crosslinking agent to the value obtained by subtracting the amount of water extracted to the outside by the primary drying step from the amount of water contained in the first and second aqueous liquids prior to polymerization (the amount of water of the primary dried gel), as the amount of water of the water-containing gelated polymer, followed by calculating the ratio of the above-mentioned amount of water of the water-containing gelated polymer to the weight of components derived from the water-soluble ethylenically unsaturated monomer that composes the water-containing gelated polymer.

The weight of components derived from the water-soluble ethylenically unsaturated monomer that composes the water-containing gelated polymer is determined by calculating as the theoretical polymer solid fraction from the total weight of the water-soluble ethylenically unsaturated monomer used in the polymerization reaction.

When mixing the water-containing gelated polymer and the post-crosslinking agent, water or a hydrophilic solvent may be added as a solvent that dissolves the post-crosslinking agent in order to uniformly disperse the post-crosslinking agent. Examples of hydrophilic solvents include lower alcohols such as methyl alcohol, ethyl alcohol and isopropyl alcohol; ketones such as acetone and methyl ethyl ketone; ethers such as dioxane and tetrahydrofuran; amides such as N,N-dimethylformamide; and, sulfoxides such as dimethylsulfoxide. One type of each of these solvents may be used alone or two or more types may be used in combination as necessary.

From the viewpoint of uniformly dispersing the post-crosslinking agent while enhancing process economy by rationally shortening the drying step, the weight ratio of the amount of water of the primary dried gel and the amount of solvent added may be 100:0 to 60:40, 99:1 to 70:30, 98:2 to 80:20 or 98:2 to 90:10.

The reaction temperature of the post-crosslinking reaction may be 60° C. or higher, 70° C. to 200° C. or 80° C. to 150° C. As a result of making the reaction temperature to be 60° C. or higher, there is a tendency that the crosslinking reaction is accelerated and the reaction does not require an excessive amount of time, while as a result of making the reaction temperature to be 200° C. or lower, deterioration of the resulting water-absorbent resin particle and a decrease in water-absorption performance tend to be able to be inhibited.

Although the reaction time of the post-crosslinking reaction cannot be uniformly determined since it varies according to the reaction temperature, type and amount of the post-crosslinking agent and the like, it may be normally 1 minute to 300 minutes or 5 minutes to 200 minutes.

Production Method 3 may also be provided with a secondary drying step for further removing water, the hydrocarbon dispersion medium and the like by distillation of applying energy such as heat from the outside after having carried out the post-crosslinking reaction. Carrying out this secondary drying step tends to allow the obtaining of a water-absorbent resin particle having more superior fluidity.

There are no particular limitations on the method of the secondary drying step, and examples thereof include: (a) a method in which water and the hydrocarbon dispersion medium are simultaneously removed by distilling a mixture of resin particles dispersed in the hydrocarbon dispersion medium after the post-crosslinking reaction, (b) a method in which resin particles are removed by decantation and then dried under reduced pressure, and (c) a method in which resin particles are filtered out with a filter and dried under reduced pressure. Among these, the method of (a) can be employed in consideration of simplicity of the production process.

According to Production Method 3, a water-absorbent resin particle according to the present embodiment described above can be obtained. The resulting water-absorbent resin particle has a low residual volatile component content while having a particle size of a suitable size and a superior water-absorption rate.

Use of the resulting water-absorbent resin particle obtained in the manner described above allows the obtaining of an absorbent material, absorbent article and water blocking material and the like as described below.

The absorbent material according to the present embodiment contains the above-mentioned water-absorbent resin particle and hydrophilic fibers. Examples of hydrophilic fibers include cellulose fibers such as flocculent pulp and chemical pulp, and artificial cellulose fibers such as rayon and acetate fibers. The absorbent material may also further contain synthetic fibers composed of a synthetic resin such as polyamide, polyester and polyolefin as a reinforcing material. Examples of the structure of the absorbent material include a mixed structure in which the water-absorbent resin particle is uniformly blended with the hydrophilic fibers, a sandwich structure in which the water-absorbent resin particles is retained between a plurality of layers of the hydrophilic fibers, and a structure in which the water-absorbent resin particle and the hydrophilic fibers are wrapped around a liquid-permeable sheet such as tissue paper or non-woven fabric. However, the absorbent material of the present embodiment is not limited to that exemplified here.

The amount of the water-absorbent resin particle used in the absorbent material may be, for example, 5% by weight to 80% by weight, 10% by weight to 70% by weight or 15% by weight to 60% by weight based on the weight of the absorbent material. As a result of making the amount of the water-absorbent resin particle used to be 5% by weight or more, the absorption capacity of the absorbent material tends to increase and leakage and re-wetting tend to be able to be inhibited. As a result of making the amount of the water-absorbent resin particle used to be 80% by weight or less, the cost of the absorbent material can be reduced and the feel of the absorbent material becoming hard tends to be able to be inhibited.

FIG. 1 is a cross-sectional view showing an embodiment of an absorbent article. An absorbent article 30 according to the present embodiment is provided with a liquid-permeable sheet 10, a liquid-impermeable sheet 20 and an absorbent material 15. The absorbent material 15 includes a hydrophilic fiber layer 13 formed of hydrophilic fibers and water-absorbent resin particles 5 arranged in a hydrophilic fiber layer 13. The absorbent material 15 is arranged between the liquid-permeable sheet 10 and the liquid-impermeable sheet 20 that are arranged facing each other. The thickness of the absorbent material 15 may be, for example, 0.1 mm to 10 mm.

Examples of absorbent articles include disposable diapers, incontinence pads, sanitary napkins, pet sheets and absorbent drip sheets for foods. Among these, the water-absorbent resin particle according to the present invention can be used in, for example, special hygienic materials such as large-sized infant diapers, children's bedwetting pants, adult diapers, incontinence pads and heavy day sanitary napkins, pet sheets and portable toilets. In the case of using the absorbent article in a product that contacts the body, the liquid-permeable sheet is arranged on the side that contacts the body, while the liquid-impermeable sheet is arranged on the opposite side from the side that contacts the body.

Examples of the above-mentioned liquid-permeable sheet include non-woven fabrics and porous synthetic resin sheets composed of a synthetic resin such as polyethylene, polypropylene, polyester and polyamide. Examples of the above-mentioned liquid-impermeable sheet include sheets composed of a synthetic resin such as polyethylene, polypropylene and polyvinyl chloride, and sheets composed of composite materials of these synthetic resins and a non-woven fabric. The sizes of the liquid-permeable sheet and the liquid-impermeable sheet cannot be uniformly determined since they vary according to the application of the absorbent article and the like. Thus, the sizes thereof are suitably adjusted corresponding to the application of the absorbent article and the like.

Figure 2:
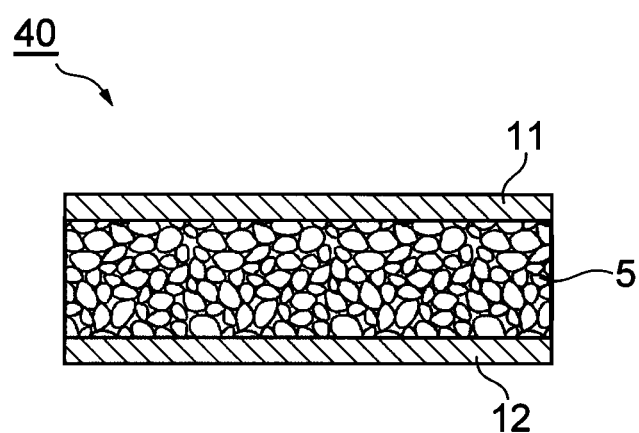
FIG. 2 is a cross-sectional view showing an embodiment of a water blocking material.

FIG. 2 is a cross-sectional view showing an embodiment of a water blocking material. A water blocking material 40 according to the present embodiment is provided with a first liquid-permeable sheet 11, a second liquid-permeable sheet 12 and a water-absorbent resin particles 5. The water-absorbent particles 5 are arranged between the first liquid-permeable sheet 11 and the second liquid-permeable sheet 12 that are arranged facing each other. The water-absorbent resin particles 5 may also be sandwiched between the first liquid-permeable sheet 11 and the second liquid-permeable sheet 12 that are arranged facing each other. The water blocking material may also be provided with three or more liquid-permeable sheets. In this case, the water-absorbent resin particle may be arranged between at least one pair of adjacently arranged liquid-permeable resin sheets. When viewed from the direction of thickness of the water blocking material 40, the water-absorbent resin particles 5 may be arranged at a ratio of 30 g/m$^2$ to 500 g/m$^2$ or 100 g/m$^2$ to 300 g/m$^2$. The thicknesses of the first liquid-permeable sheet 11 and the second liquid-permeable sheet 12 may be, for example, 0.05 mm to 6 mm.

The water blocking material according to the present embodiment is obtained by, for example, arranging a plurality of water-absorbent resin particles between a first liquid-permeable sheet and a second liquid-permeable sheet that are arranged facing each other. More specifically, the water-absorbent resin particles can be fixed to the liquid-permeable sheets using an adhesive to form the water-absorbent resin particles into a sheet. The water blocking material according to the present embodiment is used, for example, to protect the core portion of an electrical power cable or optical communications cable by being wrapped there around. The water blocking material is able to absorb water that has leaked in through a crack formed by deterioration of an external member and then swell to generate pressure within the cable, thereby making it possible to prevent the water from reaching the core portion of the cable.

A liquid-permeable sheet similar to that used in the case of the above-mentioned absorbent article can be used for the liquid-permeable sheets of the water blocking material. Examples of the above-mentioned adhesive used include rubber-based adhesives such as natural rubber-based, butyl rubber-based and polyisoprene adhesives; styrene-based elastomer adhesives such as styrene-isoprene block copolymers (SIS) and styrene-butadiene block copolymers (SBS); ethylene-vinyl acetate copolymer (EVA) adhesives; ethylene-acrylic acid derivative copolymer-based adhesives such as ethylene-ethyl acrylate copolymers (EEA); ethylene-acrylic acid copolymer (EAA) adhesives, polyamide-based adhesives such as copolymer nylon; polyolefin-based adhesives such as polyethylene and polypropylene adhesives; and polyester-based adhesives such as polyethylene terephthalate (PET) and copolymer polyester adhesives; and, acrylic adhesives.

EXAMPLES

The following provides a more detailed explanation of the present invention by listing examples thereof. However, the present invention is not limited to only these examples.

<Evaluation Methods>

(1) Residual Volatile Component Content

In the present invention, residual volatile component content is calculated from the amount of hydrocarbon dispersion medium that is used during synthesis of the water-absorbent resin particle and incorporated within the particle. Since the hydrocarbon dispersion medium incorporated within the particle during synthesis is actually strongly shielded within the resin even when in a dried state, emission to the outside is very little. A portion of the amount of residual volatile components is released when the resin particle has absorbed water and formed a gel.

The amount of residual volatile components derived from the hydrocarbon dispersion medium remaining on the water-absorbent resin particle was measured according to the procedure described below. Namely, the amount of hydrocarbon dispersion medium in a gas that has volatilized when a mixed solution of dimethylsulfoxide (DMF), 25% by weight aqueous phosphoric acid solution and the water-absorbent resin particle is heated to 110° C. was measured, and the value obtained by converting the measured value to the amount per gram of the water-absorbent resin particle was taken to be the residual volatile component content. The specific procedure is described below.

(a) Preparation of Calibration Curve

Hydrocarbon dispersion media used in the examples and comparative examples, dimethylsulfoxide (DMF) and 25% by weight aqueous phosphoric acid solution were placed in stopperable glass containers. The contents of the containers were cooled as necessary to inhibit error caused by volatilization during measurement.

First, 0.15 g of the above-mentioned hydrocarbon dispersion media were accurately weighed into a volumetric flask having an internal volume of 200 mL followed by the addition of DMF to a total volume of 200 mL for use as a Standard Solution 1. Next, the Standard Solution 1 was precisely transferred to a volumetric flask having an internal volume of 20 mL with a 10 mL volumetric pipette followed by the addition of DMF to a total volume of 20 mL to dilute the Standard Solution 1 by half for use as a Standard Solution 2.

A Standard Solution 3 was then obtained by similarly diluting the Standard Solution 2 by half, a Standard Solution 4 was then obtained by similarly diluting the Standard Solution 3 by half, a Standard Solution 5 was then obtained by similarly diluting the Standard Solution 4 by half.

4 mL of the Standard Solution 1 were then added to a vial having an internal volume of 20 mL (SMI-Lab Ltd., VZH-20CR-100) followed by further adding 5 mL of 25% by weight aqueous phosphoric acid solution. The vial was promptly sealed using a rubber septum and aluminum cap, and the contents of the vial were agitated and mixed by shaking for 1 minute. The same procedures were carried out on the Standard Solutions 2 to 5 to prepare calibration curve solutions.

After heating the above-mentioned vials for 2 hours at 110° C. while agitating by shaking, 1 mL of the gaseous phase was injected into a gas chromatograph to obtain a chromatogram for each of the calibration curve solutions. A calibration curve was then prepared by using the weights of the hydrocarbon dispersion media accurately determined when preparing the calibration curve solutions and the peak areas of the chromatograms. In the case a plurality of peaks derived from the hydrocarbon dispersion media were observed, the calibration curve was prepared by using the total peak area of those peaks.

(b) Measurement of Residual Volatile Component Content

DMF and 25% by weight aqueous phosphoric acid solution were prepared. 0.10 g of the water-absorbent resin particles obtained in the examples and comparative examples were respectively accurately weighed into vials having an internal volume of 20 mL. 4 mL of DMF and 5 mL of 25% by weight aqueous phosphoric acid solution were added to the vials. The vials were promptly sealed using a rubber septum and aluminum cap followed by mixing the contents thereof by shaking the vials for 1 minute. After heating the vials for 2 hours at 110° C. while shaking to mix the contents, 1 mL of the gaseous phase was injected into a gas chromatograph to obtain a chromatogram for the contents of each vial.

The amount of hydrocarbon dispersion medium contained in the water-absorbent resin particles (0.10 g as determined by weighing accurately) was determined from the peak area of the resulting chromatograms and the previously prepared calibration curve. The value obtained by converting the calculated value to the amount per gram of water-absorbent resin particle was taken to be the residual volatile component content (% by weight).

The following indicates the conditions of the gas chromatograph.

Apparatus: GC-2014 (Shimadzu Corp.),
head space auto-sampler: HT200H (Hamilton Company)
Packing material: Squalane 25% Shimalite (NAW) (101) 80-100 mesh
Column: 3.2 mm in diameter×2.1 m in length
Column temperature: 80° C.
Injection port temperature: 180° C.
Detector temperature: 180° C.
Detector: Flame ionization detector (FID)
Carrier gas: $N_2$
Vial heating temperature: 110° C.
Syringe set temperature: 130° C.

(2) Odor Sensory Test (6-Level Odor Intensity Indication Method)

Odor derived from the hydrocarbon dispersion medium when the water-absorbent resin particle swelled was evaluated in the manner described below. 20.0 g of 0.9% by weight aqueous sodium chloride solution (hereinafter called physiological saline) at 25° C. were added to a glass vessel with a lid (mayonnaise jar) having an internal volume of 140 mL, followed by inserting a stirrer bar having a length of 3 cm and stirring. 2.0 g of the water-absorbent resin particles were added to the glass vessel and sealed therein. Odor derived from the hydrocarbon dispersion medium present in the glass vessel was assessed by five analysts in accordance with the evaluation criteria indicated in Table 1, and the average value thereof was taken to be the odor evaluation result.

TABLE 1

| 6-Level Evaluation Scale | Evaluation Criteria |
|---|---|
| 5 | Intense odor |
| 4 | Strong odor |
| 3 | Easily perceivable odor |
| 2 | Identifiable but weak odor |
| 1 | Barely perceivable odor |
| 0 | Odorless |

(3) Water-Absorption Capacity of Physiological Saline (g/g)

The absorption capacity of physiological saline was evaluated in the manner described below. 500 g of physiological saline were mixed with 2.0 g of water-absorbent resin particles followed by stirring for 60 minutes at room temperature. The above-mentioned mixed solution was then filtered using a standard HS Z 8801-1 sieve having a weight Wa (g) and mesh size of 75 μm. The mixed solution to be filtered was allowed to stand on the sieve for 30 minutes while inclining the sieve at an inclination angle of about 30 degrees relative to horizontal. The total weight Wb (g) of the water-absorbent resin particles that had absorbed the physiological saline and the sieve was then measured and water-absorption capacity was determined using the formula indicated below.

Water-absorption capacity of physiological saline= $(Wb-Wa)/2.0$ (4) Water-Absorption Rate of Physiological Saline (Seconds)

Measurement of water-absorption rate was carried out in a room controlled to a temperature of 25° C.±1° C. 50.0±0.1 g of physiological saline adjusted to a temperature of 25° C.±0.2° C. with a constant temperature bath were stirred with a magnetic stirrer (8 mm in diameter×30 mm in length, no ring) to generate an vortex at a rotating speed of 600 rpm. 2.0±0.002 g of the water-absorbent resin particles were then added all at once to the physiological saline, the amount of time from addition of the water-absorbent resin particles until the vortex on the liquid surface converged (seconds) was measured, and that time was taken to be the water-absorption rate of the water-absorbent resin particles.

(5) Median Particle Size 0.25 g of amorphous silica (Degussa Japan, trade name: Sipernat 200) as a lubricant was mixed with 50 g of the water-absorbent resin particles. The water-absorbent resin particles mixed with the lubricant were passed through a standard JIS Z 8801-1 sieve having a mesh size of 250 μm. Median particle size was measured using the combination of sieves as indicated in (A) below in the case the amount of resin particles that remained on the sieve with respect to the total amount thereof was 50% by weight or more, while the combination of sieves as indicated in (B) below was used in the case the amount of resin particles remaining on the sieve was less than 50% by weight.

(A) JIS standard sieves were combined in a downward order of a sieve having a mesh size of 850 μm, sieve having a mesh size of 600 μm, sieve having a mesh size of 500 μm, sieve having a mesh size of 425 μm, sieve having a mesh size of 300 μm, sieve having a mesh size of 250 μm, sieve having a mesh size of 150 μm and tray.

(B) JIS standard sieves were combined in a downward order of a sieve having a mesh size of 425 μm, sieve having a mesh size of 250 μm, sieve having a mesh size of 180 μm, sieve having a mesh size of 150 μm, sieve having a mesh size of 106 μm, sieve having a mesh size of 75 μm, sieve having a mesh size of 45 μm and tray.

The above-mentioned water-absorbent resin particles were placed on the uppermost sieve and classified by shaking for 20 minutes using a Ro-Tap shaker.

After classifying, the weight of the water-absorbent resin particles remaining on the sieve was calculated as a weight percentage based on total weight, and by integrating those values in order starting with the largest particle size, the relationship between sieve mesh size and the integrated values of the weight percentages of water-absorbent resin particles that remained on the sieves was plotted on logarithmic probability paper. The particle size corresponding to the 50% by weight value of the integrated weight percentages was taken to be the median particle size by connecting the plotted points on the probability paper with a straight line.

(6) Specific Surface Area ($m^2/g$)

The water-absorbent resin particles used to measure specific surface area were passed through a 42 mesh standard HS Z 8801-1 sieve (mesh size: 355 μm) to adjust a particle size thereof to be retained on an 80 mesh standard sieve (mesh size: 180 μm). Next, this sample was dried for 16 hours at a temperature of 100° C. under reduced pressure of about 1 Pa with a vacuum dryer. Subsequently, the adsorption isotherm at −196° C. was measured using krypton gas for the adsorption gas with a high-precision fully-automated gas adsorption system (trade name: BELSORP 36, BEL Japan, Inc.), and specific surface area was determined from a multi-point BET plot.

(7) Handling Property

Powder handling property of the water-absorbent resin particles was evaluated visually by five analysts in accordance with the criteria indicated below. Evaluations selected by three or more analysts were taken to represent the powder handling property of the water-absorbent resin particles.

Good: Low dusting, suitably fluidity, ease of weighing, cleaning and other manipulation Poor: Large amount of dusting, low fluidity, difficulty in weighing, cleaning and other manipulation (8) Swelling Capacity (mm)

0.2 g of water-absorbent resin particles were roughly evenly spread out over the entire bottom surface of a concave, circular cup (height: 30 mm, inner diameter: 80.5 mm), and while applying a load of 90 g to the water-absorbent resin particles with a convex, circular cylinder (outer diameter: 80 mm, and having sixty through holes 7 having a diameter of 2 mm uniformly arranged on the surface that contacts the water-absorbent resin particles), the displacement (movement distance) of the convex, circular cylinder in the vertical direction relative to the bottom surface of the concave, circular cup after 1 minute and after 10 minutes when 130 g of water at 20° C. were added to the concave, circular cup was taken to represent initial swelling capacity (1 minute value) and equilibrium swelling capacity (10 minute value), respectively.

Figure 3:
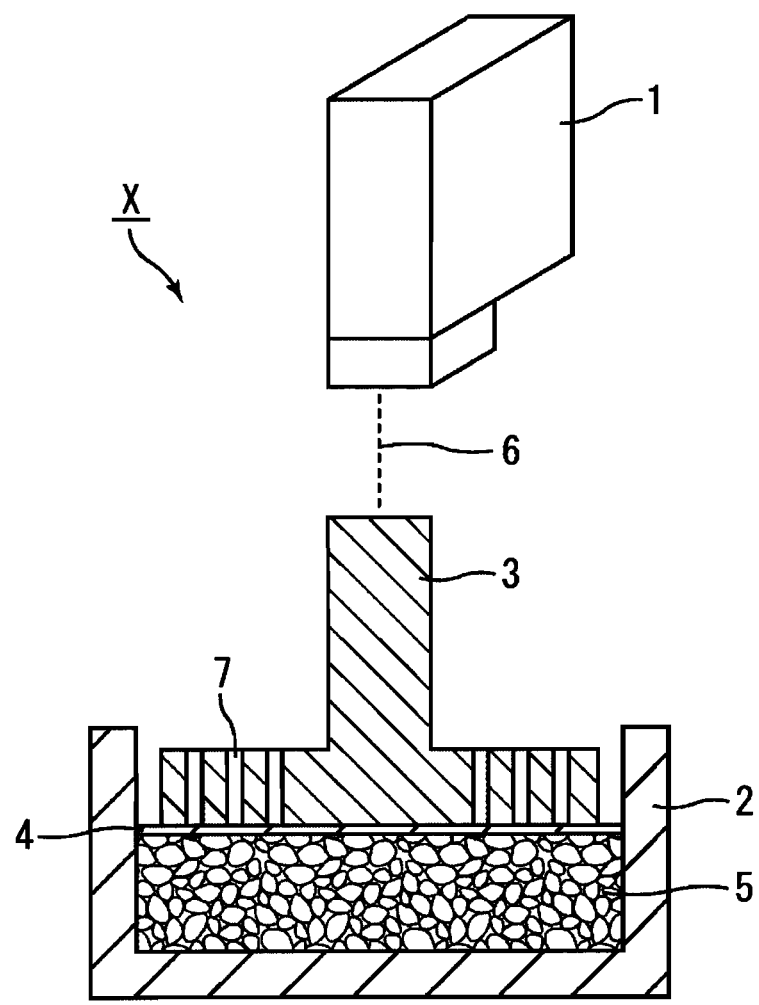
FIG. 3 is a schematic diagram showing an apparatus for measuring swelling capacity.

Swelling capacity was measured in the manner described below using an apparatus for measuring swelling capacity. A diagram of the apparatus used to measure swelling capacity is shown in FIG. 3. An apparatus X used to measure swelling capacity as shown in FIG. 3 is composed of a movement distance measuring unit 1, a concave, circular cup 2, a plastic convex, circular cylinder 3 and a non-woven fabric 4 (liquid-permeable non-woven fabric having a basis weight of 12 $g/m^2$). The swelling capacity measuring apparatus X has a sensor capable of measuring displacement of distance in 0.01 mm units with laser light 6 (located in the lower portion of the movement distance measuring unit 1). A prescribed amount of water-absorbent resin particles 5 are able to be uniformly dispersed within the concave, circular cup 2. The convex, circular cylinder 3 is able to uniformly apply a load of 90 g to the water-absorbent resin particles 5.

0.2 g of sample (water-absorbent resin particles 5) were uniformly dispersed in the concave, circular cup 2 and then covered with the non-woven fabric 4. The convex, circular cylinder 3 was then gently placed on the non-woven fabric 4, and the laser light 6 of the sensor of the movement distance measuring unit 1 was positioned so as to irradiate the center of the convex portion of the convex, circular cylinder 3. 130 g of ion exchange water preliminarily adjusted to 20° C. were placed in the concave, circular cup 2, and the distance the convex, circular cylinder 3 was pushed up by swelling of the water-absorbent resin particles 5 was measured. The movement distances of the convex, circular cylinder 3 at 1 minute and 10 minutes after the start of water absorption were taken to represent initial swelling capacity (1 minute value) and equilibrium swelling capacity (10 minute value), respectively. The ratio (initial swelling ratio) of initial swelling capacity (1 minute value) to equilibrium swelling capacity (10 minute value) was then calculated.

(9) Aqueous Liquid Viscosity

Viscosity of the aqueous liquid was measured using a Brookfield rotational viscometer (LVDV-1) under conditions of a spindle rotating speed of 60 rpm and temperature of 20° C., and was calculated as the average value of two measurements. More specifically, 150 mL of the aqueous liquid were added to a cylindrical glass container used to measure viscosity having an internal volume of 170 mL, followed by immersing for 30 minutes or more in a constant temperature bath adjusted to 20° C. to bring the temperature of the aqueous liquid to 20° C. The viscosity of the aqueous liquid was measured twice using a Brookfield rotational viscometer (LVDV-1) by reading the value on the scale at 5 minutes after the start of rotation at a spindle rotating speed of 60 rpm. The viscosity of the aqueous liquid at 20° C. was then determined by multiplying a coefficient corresponding to the type of spindle by the average value of the measurement results. The spindle was suitably selected according to the viscosity of the aqueous liquid measured.

<Study 1>

Example 1

A round-bottom cylindrical separable flask (to be referred to as a round-bottom flask) having an inner diameter of 100 mm and provided with a reflux condenser, a dropping funnel, a nitrogen gas inlet tube and a stirrer (coated on the surface of the fluorine resin) which was provided with two levels of four inclined paddle blades having a blade diameter of 50 mm was prepared. The round-bottom flask was charged with 660 mL of n-heptane as a hydrocarbon dispersion medium, and 1.10 g of sorbitan monolaurate (NOF Corp., trade name: Nonion LP-20R, HLB: 8.6) as a surfactant. The temperature was raised to 45° C. to dissolve the surfactant in the n-heptane.

On the other hand, 92 g (1.03 mol) of an 80.5% by weight aqueous acrylic acid solution as water-soluble ethylenically unsaturated monomer were added to a beaker having an internal volume of 300 mL. 147.7 g of 20.9% by weight aqueous sodium hydroxide solution was dropped into the beaker while cooling the aqueous acrylic acid solution with ice to neutralize 75 mol % of the acrylic acid. Subsequently, 1.10 g of polyvinyl alcohol (Nippon Synthetic Chemical Industry Co., Ltd., trade name: GH-20, weight average molecular weight: 1,300,000, degree of saponification: 88) as a hydrophilic polymeric dispersion agent and 0.10 g (0.00037 mol) of potassium persulfate as a radical polymerization initiator were added to the beaker and dissolved to prepare an aqueous liquid. The polymer solid fraction of this aqueous liquid was 91 g and the amount of water was 148.6 g.

The entire amount of the above-mentioned aqueous liquid was added to the above-mentioned round-bottom flask while stirring at a stirrer rotating speed of 700 rpm. After having replaced the inside of the system with nitrogen for 30 minutes, the round-bottom flask was immersed in a water bath at 70° C. to heat the system followed by carrying out a polymerization reaction for 1 hour to obtain a water-containing gelated polymer.

Next, the reaction system was heated using an oil bath at 120° C., and 111.7 g of water were extracted outside the system while refluxing the n-heptane by azeotropy of the water and n-heptane (primary drying step). Subsequently, 4.14 g (0.00048 mol) of 2% by weight aqueous ethylene glycol diglycidyl ether solution as a post-crosslinking agent was added to the round-bottom flask to obtain a mixture containing the post-crosslinking agent. The amount of water in the round-bottom flask at this time was 40.9 g, and the water content of the water-containing gelated polymer after primary drying (during post-crosslinking) was 45% by weight. After preparing the mixture containing the post-crosslinking agent, it was held for 2 hours at about 80° C. (post-crosslinking step).

Subsequently, n-heptane was evaporated to dryness at 120° C., and 89.2 g of granular water-absorbent resin particles were obtained.

Example 2

The round-bottom flask having the same configuration as that used in Example 1 was charged with 660 mL of n-heptane as a hydrocarbon dispersion medium, and 1.10 g of sorbitan monolaurate (NOF Corp., trade name: Nonion LP-20R, HLB: 8.6) as a surfactant. The temperature was raised to 45° C. to dissolve the surfactant in the n-heptane.

On the other hand, 92 g (1.03 mol) of 80.5% by weight aqueous acrylic acid solution as a water-soluble ethylenically unsaturated monomer was added to a beaker having an internal volume of 300 mL. 147.7 g of 20.9% by weight aqueous sodium hydroxide solution was dropped into the beaker while cooling the aqueous acrylic acid solution with ice to neutralize 75 mol % of the acrylic acid. Subsequently, 0.46 g of hydroxyethyl cellulose (Sumitomo Seika Chemicals Co., Ltd., trade name: AW-15F) as a water-soluble thickener and 0.10 g (0.00037 mol) of potassium persulfate as a radical polymerization initiator were added to the beaker and dissolved to prepare an aqueous liquid. The viscosity of this aqueous liquid at 20° C. was 40 mPa·s, and the polymer solid fraction of this aqueous liquid was 91 g and the amount of water was 148.6 g.

The entire amount of the above-mentioned aqueous liquid was added to the above-mentioned round-bottom flask while stirring at a stirrer rotating speed of 700 rpm. After having replaced the inside of the system with nitrogen for 30 minutes, the round-bottom flask was immersed in a water bath at 70° C. to heat the system followed by carrying out a polymerization reaction for 1 hour and 30 minutes to obtain a water-containing gelated polymer.

Next, the reaction system was heated using an oil bath at 120° C., and 111.7 g of water were extracted outside the system while refluxing the n-heptane by azeotropy of the water and n-heptane (primary drying step). Subsequently, 4.14 g (0.00048 mol) of 2% by weight aqueous ethylene glycol diglycidyl ether solution as a post-crosslinking agent was added to the round-bottom flask to obtain a mixture containing the post-crosslinking agent. The amount of water in the round-bottom flask at this time was 40.9 g, and the water content of the water-containing gelated polymer after primary drying (during post-crosslinking) was 45% by weight. After preparing the mixture containing the post-crosslinking agent, it was held for 2 hours at about 80° C. (post-crosslinking step).

Subsequently, n-heptane was evaporated to dryness at 120° C. (secondary drying step), and 87.1 g of granular water-absorbent resin particles were obtained.

Example 3

The round-bottom flask having the same configuration as that used in Example 1 was charged with 580 mL of n-heptane as a hydrocarbon dispersion medium, and 0.97 g of sorbitan monolaurate (NOF Corp., trade name: Nonion LP-20R, HLB: 8.6) as a surfactant. The temperature was raised to 45° C. to dissolve the surfactant in the n-heptane.

On the other hand, 81.0 g (0.91 mol) of 80.5% by weight aqueous acrylic acid solution as a water-soluble ethylenically unsaturated monomer was added to a beaker having an internal volume of 300 mL. 130.0 g of 20.9% by weight aqueous sodium hydroxide solution was dropped into the beaker while cooling the aqueous acrylic acid solution with ice to neutralize 75 mol % of the acrylic acid. Subsequently, 0.09 g (0.00033 mol) of potassium persulfate as a radical polymerization initiator was added to the beaker and dissolved to prepare a first aqueous liquid. The polymer solid fraction of this first aqueous liquid was 80.1 g and the amount of water was 130.8 g.

The entire amount of the above-mentioned first aqueous liquid was added to the above-mentioned round-bottom flask while stirring at a stirrer rotating speed of 700 rpm. After having replaced the inside of the system with nitrogen for 30 minutes, the round-bottom flask was immersed in a water bath at 70° C. to heat the system followed by carrying out a polymerization reaction for 1 hour to obtain a water-containing gelated polymer (first polymerization step). Following polymerization, 0.36 g (0.000042 mol) of 2% by weight aqueous ethylene glycol diglycidyl ether solution as an intermediate crosslinking agent was added followed by carrying out a crosslinking reaction at 75° C. for 30 minutes (intermediate crosslinking step).

Next, separate from the above-mentioned first polymerization step, 81.0 g (0.91 mol) of 80.5% by weight aqueous acrylic acid solution as a water-soluble ethylenically unsaturated monomer was added to a beaker having an internal volume of 300 mL. 101.0 g of 26.9% by weight aqueous sodium hydroxide solution were dropped into the beaker while cooling the aqueous acrylic acid solution with ice to neutralize 75 mol % of the acrylic acid. Subsequently, 0.09 g (0.00033 mol) of potassium persulfate as a radical polymerization initiator was added to the beaker and dissolved to prepare a second aqueous liquid. The polymer solid fraction of this second aqueous liquid was 80.1 g and the amount of water was 102.0 g.

The suspension obtained following completion of the crosslinking reaction by the intermediate crosslinking agent was cooled to 70° C. while stirring at a stirrer rotating speed of 1,000 rpm. After dropping the entire amount of the above-mentioned second aqueous liquid into the cooled round-bottom flask, the inside of the reaction system was replaced with nitrogen gas for 30 minutes while holding the temperature inside the reaction system to the temperature at completion of dropping (55° C.). The reaction system was then heated by immersing the round-bottom flask in a water bath at 70° C. followed by carrying out polymerization for 1 hour (second polymerization step) to obtain a water-containing gelated polymer.

The suspension containing the water-containing gelated polymer obtained by going through the second polymerization step was heated by immersing the round-bottom flask in an oil bath at 120° C., and 175.6 g of water were extracted outside the system while refluxing the n-heptane by azeotropy of the water and n-heptane (primary drying step). Subsequently, 7.29 g (0.00084 mol) of 2% by weight aqueous ethylene glycol diglycidyl ether solution as a post-crosslinking agent was added to the round-bottom flask to obtain a mixture containing the post-crosslinking agent. The amount of water in the round-bottom flask at this time was 64.7 g. The water content of the water-containing gelated polymer after primary drying (during post-crosslinking) was 40% by weight. After preparing the mixture containing the post-crosslinking agent, it was held for 2 hours at about 80° C. (post-crosslinking step).

Subsequently, n-heptane was evaporated to dryness at 120° C. (secondary drying step), and 161.3 g of granular water-absorbent resin particles were obtained.

Example 4

160.8 g of granular water-absorbent resin particles were obtained by carrying out the same procedure as Example 3 with the exception of further adding 0.81 g of polyvinyl alcohol (Nippon Synthetic Chemical Industry Co., Ltd., trade name: GH-20, weight average molecular weight: 1,300,000, degree of saponification: 88) to the aqueous liquid of the first polymerization step. The water content of the water-containing gelated polymer after primary drying (during post-crosslinking) was 40% by weight.

Comparative Example 1

Complying with Example 6 of Japanese Patent Application Laid-open No. S56-131608

213 g of cyclohexane as a hydrocarbon dispersion medium and 1.9 g of sorbitan monolaurate (NOF Corp., trade name: Nonion LP-20R, HLB: 8.6) as a surfactant were added to a 500 mL four-mouth, round-bottom flask equipped with a stirrer, a reflux condenser, a dropping funnel and a nitrogen gas inlet tube. After dissolving the surfactant in the cyclohexane at room temperature while stirring, nitrogen gas was blown in to remove dissolved oxygen.

On the other hand, 48.8 g (0.542 mol) of 80% by weight aqueous acrylic acid solution as a water-soluble ethylenically unsaturated monomer was added to an Erlenmeyer flask having an internal volume of 200 mL. 67.0 g of a 25.9% by weight aqueous sodium hydroxide solution was dropped into the Erlenmeyer flask while cooling the aqueous acrylic acid solution with ice from the outside to neutralize 80 mol % of the acrylic acid. Subsequently, 0.13 g (0.00048 mol) of potassium persulfate as a radical polymerization initiator was added to the Erlenmeyer flask and dissolved to prepare an aqueous liquid. The polymer solid fraction of this aqueous liquid was 48.6 g and the amount of water was 67.1 g.

The entire amount of the above-mentioned aqueous liquid was added to the above-mentioned four-mouth, round-bottom flask while stirring at a stirrer rotating speed of 700 rpm. After having adequately replaced the inside of the system with nitrogen, the four-mouth, round-bottom flask was immersed in a water bath at 55° C. to 60° C. to heat the system followed by carrying out a polymerization reaction for 3 hours. Following polymerization, 0.1 g (0.00057 mol) of ethylene glycol diglycidyl ether as a post-crosslinking agent was added followed by distilling off the water and cyclohexane and drying to obtain 48.3 g of fine granular water-absorbent resin particles.

Comparative Example 2

Complying with Example 1 of Japanese Patent Application Laid-Open No. H9-151224

580 mL of n-heptane as a hydrocarbon dispersion medium and 0.97 g of sorbitan monolaurate (NOF Corp., trade name: Nonion LP-20R, HLB: 8.6) as a surfactant were added to a round-bottom flask having the same configuration as that of Example 1, followed by heating to 50° C. and dissolving the surfactant in the n-heptane. Subsequently, the internal temperature of the round-bottom flask was cooled to 30° C.

On the other hand, 92 g (1.02 mol) of 80% by weight aqueous acrylic acid solution as a water-soluble ethylenically unsaturated monomer was added to an Erlenmeyer flask having an internal volume of 500 mL. 152.6 g of 20.1% by weight aqueous sodium hydroxide solution were dropped into the Erlenmeyer flask while cooling the aqueous acrylic acid solution with ice to neutralize 75 mol % of the acrylic acid. Subsequently, 0.11 g (0.00041 mol) of potassium persulfate as a radical polymerization initiator was added to the Erlenmeyer flask and dissolved to prepare an aqueous liquid. 18.4 g of water-absorbent resin particles having a water-absorption rate of 42 seconds (Sumitomo Seika Chemicals Co., Ltd., AquaKeep SA605) were added to this aqueous liquid.

Next, the entire amount of the above-mentioned aqueous liquid in the Erlenmeyer flask was added to the above-mentioned four-mouth flask and dispersed therein, and after replacing the inside of the system with nitrogen, the system was heated by immersing the four-mouth flask in a water bath at 70° C. followed by carrying out a polymerization reaction for 3 hours. Following polymerization, the reaction system was dried by distilling off the water and n-heptane to obtain 115.7 g of water-absorbent resin particles.

Comparative Example 3

92.0 g (1.02 mol) of 80% by weight aqueous acrylic acid solution as a water-soluble ethylenically unsaturated monomer was added to an Erlenmeyer flask having an internal volume of 500 mL. 102.2 g of 30% by weight aqueous sodium hydroxide solution was dropped into the Erlenmeyer flask while cooling the aqueous acrylic acid solution and stirring to neutralize 75 mol % of the acrylic acid. Subsequently, 0.11 g (0.00041 mol) of potassium persulfate as a radical polymerization initiator, 8.3 mg (0.048 mmol) of ethylene glycol diglycidyl ether as a crosslinking agent and 43.6 g of ion exchange water were added to the Erlenmeyer flask to prepare a first aqueous liquid.

334 g of n-heptane as a hydrocarbon dispersion medium was added to a five-mouth, cylindrical round-bottom flask (to be referred to as a round-bottom flask) having an internal volume of 2 L and provided with a stirrer which was provided with two levels of inclined paddle blades having a blade diameter of 50 mm, a thermometer, a reflux condenser and a nitrogen gas inlet tube and followed by heating to 61° C. The entire amount of the above-mentioned first aqueous liquid was added all at once thereto using a funnel while stirring at a stirring speed of 500 rpm, and the aqueous liquid was dispersed by stirring for 10 minutes at an internal temperature of 40° C.

Next, 0.92 g of sucrose fatty acid ester (Mitsubishi-Kagaku Foods Corp., trade name: S-370, HLB: 3.0) as a surfactant was mixed with 8.28 g of n-heptane as a hydrocarbon dispersion medium followed by heating and dissolving to obtain an oily liquid. The entire amount of this oily liquid was added to the above-mentioned round-bottom flask using a funnel followed by further dispersing the first aqueous liquid to obtain a suspension.

After adequately replacing the inside of the reaction system with nitrogen while holding the internal temperature of the round-bottom flask at 40° C., the round-bottom flask was heated for 1 hour using a water bath at 70° C. to carry out a polymerization reaction (first polymerization step). Following completion of the first polymerization step, the internal temperature of the round-bottom flask was cooled to around 21° C. while stirring at a stirring speed of 1,000 rpm.

128.8 g (1.43 mol) of 80% by weight acrylic acid as a water-soluble ethylenically unsaturated monomer was added to an Erlenmeyer flask having an internal volume of 500 mL. 142.9 g of 30% by weight aqueous sodium hydroxide solution was dropped in while cooling the aqueous acrylic acid solution from the outside and stirring to neutralize 75 mol % of the acrylic acid. Subsequently, 0.15 g (0.00055 mol) of potassium persulfate as a radical polymerization initiator, 11.6 mg (0.067 mmol) of ethylene glycol diglycidyl ether as a crosslinking agent and 16.7 g of distilled water were added to the Erlenmeyer flask to prepare a second aqueous liquid.

Next, the entire amount of the above-mentioned second aqueous liquid was added to the cooled suspension obtained after the first polymerization step with a dropping funnel, and after adequately replacing the inside of the reaction system with nitrogen, the reaction system was heated for 1 hour by immersing the round-bottom flask in a water bath at 70° C. to carry out a polymerization reaction (second polymerization step).

Following the polymerization reaction of the second polymerization step, the round-bottom flask was immersed in an oil bath at 120° C., the suspension was heated and 260 g of water was extracted outside the system while refluxing the n-heptane by azeotropic distillation. As a result, a dehydrated polymer was obtained that was dispersed in n-heptane. 8.2 g (0.00094 mol) of 2% by weight aqueous ethylene glycol diglycidyl ether solution as a post-crosslinking agent was added to the resulting heptane-dispersed dehydrated polymer followed by carrying out a post-crosslinking reaction for 2 hours at about 80° C.

Subsequently, the round-bottom flask was immersed in an oil bath at 120° C. to heat the suspension followed by removing the n-heptane and water by distillation and drying in the presence of flowing nitrogen to obtain 234 g of water-absorbent resin particles in the form of agglomerated spherical particles.

Comparative Example 4

Complying with Comparative Example 3 of WO 97/3114

288 g of 10% by weight aqueous 2,2'-azobis(2-methylpropionamidine)dihydrochloride solution was added to a 500 mL cylindrical separable flask provided with a stirrer, followed by the addition of 53.6 g of 37% by weight aqueous sodium acrylate solution while holding the liquid temperature at 20° C. and stirring at 1,200 rpm. The mixed solution became cloudy several seconds later and a white, fine particulate solid of about 10 μm was formed from the mixed solution. The white, fine particulate solid was isolated by filtering this cloudy liquid and then purified by rinsing with water.

Next, 711 g of an aqueous monomer solution (monomer concentration: 38%) of sodium acrylate having a neutralization rate of 75 mol % for use as monomer during polymerization, 0.45 g (0.05 mol %) of trimethylolpropane triacrylate solution as a crosslinking agent, and 0.52 g of 2,2'-azobis(2-methylpropionamidine)diacrylate complex obtained as the above-mentioned white, fine particulate solid as a foaming agent were added to an SUS container having an internal volume of 2 L followed by uniformly dispersing and bringing to a liquid height of about 5 cm. After replacing the inside of the SUS container with nitrogen, 3.1 g of a 10% by weight aqueous ammonium persulfate solution and 1.56 g of 1% by weight L-ascorbic acid solution as a radical polymerization initiator were added followed by stirring and uniformly dispersing, after which polymerization began one minute later.

A large number of fine bubbles were uniformly contained in the resulting white, water-containing gelated polymer. The water-containing gelated polymer was cut to about 10 mm and spread out over a 300 μm wire mesh followed by drying with hot air for 60 minutes at 150° C. The dried product was crushed using a metal blender and further classified with an 850 μm mesh to obtain a water-absorbent resin precursor.

30 g of the water-absorbent resin precursor were weighed into a round-bottom, separable flask having an inner diameter of 100 mm and provided with a stirrer (to be referred to as a round-bottom flask), and an aqueous crosslinking agent solution comprised of a mixture of 0.045 g of ethylene glycol diglycidyl ether, 1.2 g of water and 0.3 g of ethyl alcohol was sprayed onto the resin while stirring the resin. The resulting mixture was further subjected to heat treatment for 30 minutes at 180° C. with an oil bath to obtain water-absorbent resin particles.

<Evaluation>

The water-absorbent resin particles obtained in Examples 1 to and Comparative Examples 1 to 4 were evaluated for water-absorption capacity of physiological saline, water-absorption rate of physiological saline, median particle size, residual volatile component content, odor and specific surface area. The evaluation results are shown in Table 2.

TABLE 2

| | Water-absorption capacity g/g | Water-absorption rate sec | Median particle size μm | Residual volatile component content % by weight | Odor | Specific surface area m²/g |
|---|---|---|---|---|---|---|
| Ex. 1 | 63 | 4 | 330 | 0.65 | 1.6 | 0.158 |
| Ex. 2 | 65 | 2 | 160 | 0.85 | 1.8 | 0.154 |
| Ex. 3 | 60 | 2 | 150 | 0.83 | 1.8 | 0.153 |
| Ex. 4 | 56 | 3 | 220 | 0.44 | 1.4 | 0.143 |
| Comp. Ex. 1 | 85 | 3 | 140 | 1.87 | 3.2 | 0.168 |
| Comp. Ex. 2 | 63 | 22 | 330 | 1.64 | 3.0 | 0.068 |
| Comp. Ex. 3 | 58 | 28 | 310 | 0.13 | 1.0 | 0.042 |
| Comp. Ex. 4 | 45 | 30 | 300 | — | 2.0 | 0.037 |

As shown in Table 2, the water-absorbent resin particles obtained in Examples 1 to 4 all demonstrated fast water-absorption rates, low residual volatile component contents and little odor following water absorption while having a suitable particle size. In addition, the water-absorbent resin particles obtained in Examples 1 to 4 also had favorable handling property. On the other hand, the water-absorbent resin particles obtained in Comparative Examples 1 to 4 were found to be unable to adequately realize these levels of performance. The reason why a certain degree or higher of odor was perceived even for those resin particles (Comparative Example 4) obtained by aqueous polymerization that does not incorporate a hydrocarbon dispersion medium during polymerization is presumed to be the result of the presence of residual surface-crosslinking agents and residual organic solvents used during dispersion thereof.

<Study 2>

Example 5

530 mL of n-heptane as a hydrocarbon dispersion medium was added to a round-bottom flask having the same configuration as that of Example 1 followed by the addition of 1.65 g of sorbitan monolaurate (NOF Corp., trade name: Nonion LP-20R, HLB: 8.6) as a surfactant and heating to 45° C. to dissolve the surfactant.

On the other hand, 92 g (1.03 mol) of 80.5% by weight aqueous acrylic acid solution as a water-soluble ethylenically unsaturated monomer was added to a beaker having an internal volume of 300 mL. 147.6 g of 20.9% by weight aqueous sodium hydroxide solution was dropped into the beaker while cooling the aqueous acrylic acid solution with ice to neutralize 75 mol % of the acrylic acid. Subsequently, 0.10 g (0.0037 mol) of potassium persulfate as a radical polymerization initiator was added to the beaker and dissolved to prepare a first aqueous liquid. The polymer solid fraction of this first aqueous liquid was 91.0 g and the amount of water was 148.5 g.

The entire amount of the first aqueous liquid was added to the above-mentioned round-bottom flask while stirring at a stirrer rotating speed of 500 rpm. After having replaced the inside of the system with nitrogen for 30 minutes, the round-bottom flask was immersed in a water bath at 70° C. to heat the system followed by carrying out a polymerization reaction for 1 hour to obtain a water-containing gelated polymer (first polymerization step). Following polymerization, 1.24 g (0.00014 mol) of 2% by weight aqueous ethylene glycol diglycidyl ether solution as an intermediate crosslinking agent was added followed by carrying out a crosslinking reaction at 75° C. for 30 minutes (intermediate crosslinking step).

Next, separate from the above-mentioned first polymerization step, 92 g (1.03 mol) of 80.5% by weight aqueous acrylic acid solution as a water-soluble ethylenically unsaturated monomer was added to a beaker having a volume of 300 mL. 114.7 g of 26.9% by weight aqueous sodium hydroxide solution was dropped into the beaker while cooling the aqueous acrylic acid solution with ice to neutralize 75 mol % of the acrylic acid. Subsequently, 0.10 g (0.0037 mol) of potassium persulfate as a radical polymerization initiator was added to the beaker and dissolved to prepare a second aqueous liquid. The polymer solid fraction of this second aqueous liquid was 91.0 g and the amount of water was 115.9 g.

The suspension obtained following completion of the crosslinking reaction by the intermediate crosslinking agent was cooled to 65° C. while stirring at a stirrer rotating speed of 1,000 rpm. After dropping the entire amount of the above-mentioned second aqueous liquid into the cooled round-bottom flask, the inside of the reaction system was replaced with nitrogen gas for 30 minutes while holding the temperature inside the reaction system to the temperature at completion of dropping (50° C.). The reaction system was then heated by immersing the round-bottom flask in a water bath at 70° C. followed by carrying out polymerization for 1 hour (second polymerization step) to obtain a water-containing gelated polymer.

The suspension containing the water-containing gelated polymer obtained in the second polymerization step was heated by immersing the round-bottom flask in an oil bath at 120° C., and 208.6 g of water were extracted outside the system while refluxing the n-heptane by azeotropy of the water and n-heptane (primary drying step). Subsequently, 8.28 g (0.00095 mol) of 2% by weight aqueous ethylene glycol diglycidyl ether solution as a post-crosslinking agent was added to the round-bottom flask to obtain a mixture containing the post-crosslinking agent. The amount of water in the round-bottom flask at this time was 65.1 g, and the water content of the water-containing gelated polymer after primary drying (during post-crosslinking) was 36% by weight. After preparing the mixture containing the post-crosslinking agent, it was held for 2 hours at about 80° C. (post-crosslinking step).

Subsequently, n-heptane was evaporated to dryness at 120° C. (secondary drying step), and 190.6 g of granular water-absorbent resin particles were obtained.

Example 6

161.8 g of granular water-absorbent resin particles were obtained by carrying out the same procedure as Example 3 with the exception of making the cooling temperature of the suspension obtained following completion of the crosslinking reaction by the intermediate crosslinking agent in the first polymerization step to be 75° C. and making the system internal (suspension) temperature following dropping of the second aqueous liquid in the second polymerization step to be 60° C.

Comparative Example 5

660 mL of n-heptane as a hydrocarbon dispersion medium was added to a round-bottom flask having the same configuration as that used in Example 1 followed by the addition of 1.10 g of sorbitan monolaurate (NOF Corp., trade name: Nonion LP-20R, HLB: 8.6) as a surfactant and heating to 45° C. to dissolve the surfactant.

On the other hand, 92 g (1.03 mol) of 80.5% by weight aqueous acrylic acid solution as a water-soluble ethylenically unsaturated monomer was added to a beaker having an internal volume of 300 mL. 147.7 g of 20.9% by weight aqueous sodium hydroxide solution was dropped into the beaker while cooling the aqueous acrylic acid solution with ice to neutralize 75 mol % of the acrylic acid. Subsequently, 0.10 g (0.0037 mol) of potassium persulfate as a radical polymerization initiator was added to the beaker and dissolved to prepare an aqueous liquid. The polymer solid fraction of this aqueous liquid was 91 g and the amount of water was 148.6 g.

The entire amount of the above-mentioned aqueous liquid was added to the above-mentioned round-bottom flask while stirring at a stirrer rotating speed of 700 rpm. After having replaced the inside of the system with nitrogen for 30 minutes, the round-bottom flask was immersed in a water bath at 70° C. to heat the system followed by carrying out a polymerization reaction for 1 hour to obtain a water-containing gelated polymer.

Next, the reaction system was heated using an oil bath at 120° C., and 127.6 g of water were extracted outside the system while refluxing the n-heptane by azeotropy of the water and n-heptane (primary drying step). Subsequently, 5.52 g (0.00063 mol) of 2% by weight aqueous ethylene glycol diglycidyl ether solution as a post-crosslinking agent was added to the round-bottom flask to obtain a mixture containing the post-crosslinking agent. The amount of water in the round-bottom flask at this time was 26.3 g, and the water content of the water-containing gelated polymer after primary drying (during post-crosslinking) was 29% by weight. After preparing the mixture containing the post-crosslinking agent, it was held for 2 hours at about 80° C. (post-crosslinking step).

Subsequently, n-heptane was evaporated to dryness at 120° C. (secondary drying step), and 87.4 g of granular water-absorbent resin particles were obtained.

Comparative Example 6

189.3 g of granular water-absorbent resin particles were obtained by carrying out the same procedure as Example 5 with the exception of making the cooling temperature of the suspension obtained following completion of the crosslinking reaction by the intermediate crosslinking agent in the first polymerization step to be 40° C. and making the system internal temperature following dropping of the second aqueous liquid in the second polymerization step to be 34° C.

Comparative Example 7

92 g (1.02 mol) of 80% by weight aqueous acrylic acid solution was added to an Erlenmeyer flask having an internal volume of 500 mL. 146.0 g of a 21.0% by weight aqueous sodium hydroxide solution was dropped into the Erlenmeyer flask while cooling the aqueous acrylic acid solution with ice to neutralize 75 mol % of the acrylic acid and prepare an water-soluble ethylenically unsaturated monomer solution having a concentration of 38% by weight. 18.4 mg (106 μmol) of ethylene glycol diglycidyl ether as a crosslinking agent and 92 mg (0.00034 mol) of potassium persulfate as a radical polymerization initiator were added to the resulting water-soluble ethylenically unsaturated monomer solution for use as a first aqueous liquid. In addition, another aqueous liquid different from that described above was prepared by carrying out the same procedure as described above for use as a second aqueous liquid.

Next, 340 g (500 mL) of n-heptane as a hydrocarbon dispersion medium and 0.92 g of sucrose fatty acid ester (Mitsubishi-Kagaku Foods Corp., trade name: S-370, HLB: 3.0) as a surfactant were added to a round-bottom flask having the same configuration as that of Example 1, and after dissolving the surfactant in the n-heptane, the inside of the round-bottom flask was heated to 35° C. Subsequently, the entire amount of the first aqueous liquid was added to the round-bottom flask and suspended while holding at 35° C. and stirring followed by replacing the inside of the reaction system with nitrogen gas. The round-bottom flask was heated by immersing in a water bath at 70° C. followed by carrying out a polymerization reaction for 2 hours (first polymerization step).

Following completion of the first polymerization step, the polymer slurry was cooled to 50° C. The entire amount of the second aqueous liquid was then dropped into the reaction system with the surfactant dissolved therein. The inside of the reaction system was adequately replaced with nitrogen gas while holding the internal temperature of the system at 50° C. and stirring for 30 minutes. Subsequently, the round-bottom flask was heated by immersing in a water bath at 70° C. followed by carrying out a polymerization reaction for 1.5 hours (second polymerization step) to obtain a water-containing gelated polymer.

Next, the round-bottom flask was heated by immersing in an oil bath at 120° C., and 250 g of water was extracted outside the system while refluxing the n-heptane by azeotropy of the water and n-heptane (primary drying step). Subsequently, 110 mg (0.00063 mol) of ethylene glycol diglycidyl ether as a crosslinking agent was added to the round-bottom flask to obtain a mixture containing a post-crosslinking agent. The water content of the water-containing gelated polymer during post-crosslinking was 25% by weight. After preparing the mixture containing the post-crosslinking agent, it was held for 2 hours at about 80° C. (post-crosslinking step).

Subsequently, n-heptane was evaporated to dryness at 120° C. (secondary drying step), and 188.3 g of spherical water-absorbent resin particles were obtained.

<Evaluation>

The water-absorbent resin particles obtained in Examples 3, 5 and 6 and Comparative Examples 5 to 7 were evaluated for residual volatile component content, odor, water-absorption capacity of physiological saline, water-absorption rate of physiological saline, median particle size and handling ease. The evaluation results are shown in Table 3.

TABLE 3

|  | Surfactant HLB | Second Polymerization Step | | Residual Volatile Component | | Water-absorption capacity g/g | Water-absorption rate sec | Median particle size μm | Handling property |
|---|---|---|---|---|---|---|---|---|---|
|  |  | Suspension A temp. °C. | Suspension B temp. °C. | Content % by weight | Odor |  |  |  |  |
| Ex. 3 | 8.6 | 70 | 55 | 0.83 | 1.8 | 60 | 2 | 150 | Good |
| Ex. 5 | 8.6 | 65 | 50 | 0.94 | 2.0 | 66 | 2 | 150 | Good |
| Ex. 6 | 8.6 | 75 | 60 | 0.68 | 1.6 | 63 | 3 | 170 | Good |
| Comp. Ex. 5 | 8.6 | No second polymerization step | | 1.85 | 3.2 | 71 | 3 | 130 | Good |
| Comp. Ex. 6 | 8.6 | 40 | 34 | 1.74 | 3.0 | 64 | 4 | 280 | Good |
| Comp. Ex. 7 | 3.0 | 50 | 50 | 0.80 | 1.8 | 64 | 7 | 60 | Poor |

In Table 3, Suspension A indicates a suspension obtained after the first polymerization step but before mixing the second aqueous liquid. Suspension B indicates a suspension obtained after mixing the second aqueous liquid but before polymerization of the second polymerization step.

As shown in Table 3, the water-absorbent resin particles obtained in Examples 3, 5 and 6 were determined to all demonstrated superior water-absorption performance such as water-absorption rates as well as low residual volatile component contents while having a suitable particle size. On the other hand, the water-absorbent resin particles obtained in Comparative Examples 5 and 6 were recognized to have high residual volatile component contents and generate an odor after absorbing water. The water-absorbent resin particles obtained in Comparative Example 7 had a small particle size and had problems with powder handling ease.

<Study 3>

Example 7

88.1 g of granular water-absorbent resin particles were obtained by carrying out the same procedure as Example 2 with the exception of making the amount of hydroxyethyl cellulose added to the aqueous liquid to be 1.10 g and making the viscosity of the aqueous liquid at 20° C. to be 260 mPa·s.

Example 8

86.8 g of granular water-absorbent resin particles were obtained by carrying out the same procedure as Example 2 with the exception of adding 0.74 g of hydroxypropyl cellulose (Nippon Soda Co., Ltd., trade name: Celny H) instead of hydroxyethyl cellulose to make the viscosity of the aqueous liquid at 20° C. to be 60 mPa·s, making the amount of water extracted outside the system in the primary drying step to be 121.2 g, making the amount of the 2% by weight aqueous ethylene glycol diglycidyl ether solution added to be 5.06 g (0.00058 mol), and making the water content during the post-crosslinking reaction to be 35% by weight.

Comparative Example 8

87.4 g of granular water-absorbent resin particles were obtained by carrying out the same procedure as Example 8 with the exception of not adding hydroxypropyl cellulose and making the viscosity of the aqueous liquid at 20° C. to be 8 mPa·s.

Comparative Example 9

88.1 g of granular water-absorbent resin particles were obtained by carrying out the same procedure as Comparative Example 8 with the exception of adding 0.27 g of hydroxyethyl cellulose (Sumitomo Seika Chemicals Co., Ltd., trade name: AW-15F) and making the viscosity of the aqueous component at 20° C. to be 18 mPa·s.

<Evaluation>

The water-absorbent resin particles obtained in Examples 2, 7 and 8 and Comparative Examples 8 and 9 were evaluated for residual volatile component content, odor, water-absorption capacity of physiological saline, water-absorption rate of physiological saline, median particle size, swelling capacity and handling ease. The evaluation results are shown in Table 4.

TABLE 4

|  | Aqueous liquid viscosity mPa·s (20° C.) | Water-soluble thickener | | Residual volatile component content % by weight | Odor | Water-absorption capacity g/g | Water-absorption rate sec | Median particle size μm | Equilibrium swelling capacity mm | Initial swelling performance % | Handling property |
|---|---|---|---|---|---|---|---|---|---|---|---|
|  |  |  | parts by weight |  |  |  |  |  |  |  |  |
| Ex. 2 | 40 | HEC | 0.5 | 0.85 | 1.8 | 65 | 2 | 160 | 23.1 | 94% | Good |
| Ex. 7 | 260 | HEC | 1.2 | 0.58 | 1.4 | 66 | 4 | 240 | 24.7 | 92% | Good |
| Ex. 8 | 60 | HPC | 0.8 | 0.74 | 1.6 | 59 | 3 | 190 | 23.6 | 92% | Good |
| Comp. Ex. 8 | 8 | Not added | | 1.85 | 3.2 | 62 | 3 | 130 | 20.1 | 89% | Good |
| Comp. Ex. 9 | 18 | HEC | 0.3 | 1.81 | 3.2 | 61 | 3 | 140 | 20.3 | 83% | Good |

As shown in Table 4, the water-absorbent resin particles obtained in Examples 2, 7 and 8 were determined to have a suitable particle size, demonstrate superior water-absorption performance such as water-absorption rates while having superior handling ease, and have low residual volatile component contents. On the other hand, the water-absorbent resin particles obtained in Comparative Examples 8 and 9 were observed to have high residual volatile component contents and generate an odor after absorbing water.

<Study 4>

Examples 9 and 10

In Example 9 and 10, 88.2 g and 88.4 g, respectively, of granular water-absorbent resin particles were obtained by carrying out the same procedure as Example 1 with the exception of making the amount of polyvinyl alcohol added to the aqueous liquid to be 0.01 g and 0.67 g, respectively. The water contents of the water-containing gelated polymers after primary drying (during post-crosslinking) were both 45% by weight.

Example 11

88.3 g of granular water-absorbent resin particles were obtained by carrying out the same procedure as Example 9 with the exception of adding 0.90 g of polyvinylpyrrolidone (ISP Japan Ltd., trade name: K-90, weight average molecular weight: approx. 1,300,000) instead of polyvinyl alcohol, making the amount of water extracted outside the system in the primary drying step to be 116.1 g, and making the water content of the water-containing gelated polymer during the post-crosslinking reaction to be 40% by weight.

Example 12

88.8 g of granular water-absorbent resin particles were obtained by carrying out the same procedure as Example 11 with the exception of adding 0.90 g of polyethylene glycol (NOF Corp., trade name: PEG #20000, weight average molecular weight: approx. 20,000) instead of polyvinylpyrrolidone, making the amount of water extracted outside the system in the primary drying step to be 121.2 g, making the amount of the 2% by weight aqueous ethylene glycol diglycidyl ether solution added to be 5.06 g (0.00058 mol) and making the water content of the water-containing gelated polymer during the post-crosslinking reaction to be 35% by weight.

Comparative Example 10

87.4 g of granular water-absorbent resin particles were obtained by carrying out the same procedure as Example 12 with the exception of not adding polyethylene glycol.

Comparative Example 11

92.0 g (1.02 mol) of an 80% by weight aqueous acrylic acid solution were added to an Erlenmeyer flask having an internal volume of 500 mL. 146.0 g of a 21.0% by weight aqueous sodium hydroxide solution were dropped into the Erlenmeyer flask while cooling the aqueous acrylic acid solution with ice to neutralize 75 mol % of the acrylic acid and prepare a water-soluble ethylenically unsaturated monomer solution having a concentration of 38% by weight. 18.4 mg (106 µmol) of ethylene glycol diglycidyl ether as a crosslinking agent and 92 mg (0.00034 mol) of potassium persulfate as a radical polymerization initiator were added to the resulting water-soluble ethylenically unsaturated monomer solution for use as an aqueous liquid (a) for a first stage of reversed-phase suspension polymerization. In addition, another aqueous liquid different from that described above was prepared by carrying out the same procedure as described above for use as an aqueous liquid (b) for a second stage of reversed-phase suspension polymerization.

Next, 340 g (500 mL) of n-heptane as a hydrocarbon dispersion medium and 0.92 g of sucrose fatty acid ester (Mitsubishi-Kagaku Foods Corp., trade name: S-370, HLB: 3.0) as a surfactant were added to a five-mouth, cylindrical round-bottom flask having an internal volume of 2 L and provided with a stirrer, a two-level paddle blade, a reflux condenser, a dropping funnel and a nitrogen gas inlet tube and the surfactant was dissolved in the n-heptane followed by heating the inside of the round-bottom flask to 35° C. Subsequently, the aqueous liquid (a) was added to the round-bottom flask and suspended while holding at 35° C. and stirring followed by replacing the inside of the reaction system with nitrogen gas. The round-bottom flask was heated by immersing in a water bath at 70° C. followed by carrying out a polymerization reaction for 2 hours.

Following completion of the first stage of reversed-phase suspension polymerization, the polymer slurry was cooled to 50° C. The aqueous liquid (b) was then dropped into the reaction system with the surfactant dissolved therein. The inside of the reaction system was replaced with nitrogen gas while holding the internal temperature of the system at 50° C. and stirring for 30 minutes. Subsequently, the round-bottom flask was heated by immersing in a water bath at 70° C. followed by carrying out a polymerization reaction for 1.5 hours to obtain a water-containing gelated polymer.

Next, the round-bottom flask was heated by immersing in an oil bath at 120° C., and 250 g of water were extracted outside the system while refluxing the n-heptane by azeotropy of the water and n-heptane (primary drying step). The water content of the water-containing gelated polymer following primary drying was 25% by weight. Subsequently, 110 mg (0.00063 mol) of ethylene glycol diglycidyl ether as a post-crosslinking agent was added to the round-bottom flask to obtain a mixture containing the post-crosslinking agent. After preparing the mixture containing the post-crosslinking agent, it was held for 2 hours at about 80° C. (post-crosslinking step).

Subsequently, n-heptane was evaporated to dryness at 120° C. (secondary drying step), and 188.3 g of spherical water-absorbent resin particles were obtained.

<Evaluation>

The water-absorbent resin particles obtained in Examples 1 and 9 to 12 and Comparative Examples 10 and 11 were evaluated for residual volatile component content, odor, water-absorption capacity of physiological saline, water-absorption rate of physiological saline, median particle size, swelling capacity and handling ease. The evaluation results are shown in Table 5.

TABLE 5

| | Hydrophilic polymeric dispersion agent | | Residual volatile component content % by weight | Odor | Water-absorption capacity g/g | Water-absorption rate sec | Median particle size μm | Equilibrium swelling capacity mm | Initial swelling ratio % | Handling property |
|---|---|---|---|---|---|---|---|---|---|---|
| Ex. 9 | PVA | 0.01 | 1.28 | 2.4 | 68 | 2 | 260 | 24.2 | 92 | Good |
| Ex. 10 | PVA | 0.9 | 0.97 | 2.0 | 65 | 3 | 290 | 23.7 | 92 | Good |
| Ex. 1 | PVA | 1.5 | 0.65 | 1.6 | 63 | 4 | 330 | 22.4 | 92 | Good |
| Ex. 11 | PVP | 1.2 | 0.89 | 1.8 | 55 | 3 | 310 | 23.1 | 91 | Good |
| Ex. 12 | PEG | 1.2 | 0.98 | 2.0 | 61 | 2 | 290 | 22.2 | 91 | Good |
| Comp. Ex. 10 | Not added | | 1.85 | 3.2 | 62 | 3 | 130 | 20.1 | 89 | Good |
| Comp. Ex. 11 | Not added | | 0.80 | 1.8 | 64 | 7 | 60 | 21.2 | 60 | Poor |

As shown in Table 5, all of the water-absorbent resin particles obtained in Examples 1, 9 to 12 were determined to have a suitable particle size, demonstrate superior water-absorption performance such as water-absorption rates while having superior handling ease, and have low residual volatile component contents. On the other hand, the water-absorbent resin particles obtained in Comparative Example 10 were observed to have high residual volatile component contents and generate an odor after absorbing water. In addition, the water-absorbent resin particles obtained in Comparative Example 11 had a small particle size and had problems with handling ease.

Industrial Applicability

The water-absorbent resin particle according to the present embodiment can be used in various fields such as hygienic materials such as disposable diapers, sanitary articles and pet sheets, agricultural materials such as water-retaining materials and soil conditioners, and industrial materials such as water blocking materials for electric power or communications cables and dew-catchers, and in particular, can be preferably used in fields such as special hygienic materials such as adult diapers, incontinence pads, toilet training pants and heavy day sanitary napkins, water blocking materials for cables, pet sheets and portable toilets.

The water-absorbent resin particle obtained by the production method according to the present embodiment can be used in various fields such as hygienic materials such as disposable diapers, sanitary articles and pet sheets, agricultural materials such as water-retaining materials and soil conditioners, and industrial materials such as water blocking materials for electric power or communications cables and dew-catchers, and in particular, can be preferably used in fields such as special hygienic materials such as adult diapers, incontinence pads, toilet training pants and heavy day sanitary napkins, water blocking materials for cables, pet sheets and portable toilets.

Reference Signs List

1: movement distance measuring unit, 2: concave, circular cup, 3: convex, circular cylinder, 4: non-woven fabric, 5: water-absorbent resin particle, 6: laser light, 7: through hole, X: swelling capacity measuring apparatus, 10: liquid-permeable sheet, 11: first liquid-permeable sheet, 12: second liquid-permeable sheet, 13: hydrophilic fiber layer, 15: absorbent material, 20: liquid-impermeable sheet, 30: absorbent article, 40: water blocking material

The invention claimed is:

1. A water-absorbent resin particle, wherein a water-absorption rate of physiological saline is 1 second to 15 seconds, a median particle size is 100 μm to 600 μm, a residual volatile component content is 1.5% by weight or less, and the water-absorption rate is measured by the amount of time from addition of 2.0±0.002 g of the water-absorbent resin particles into 50.0±0.1 g of vortexed physiological saline at a rotating speed of 600 rpm until the vortex on the liquid surface converged.

2. The water-absorbent resin particle according to claim 1, wherein a specific surface area is 0.08 m$^2$/g or more.

3. The water-absorbent resin particle according to claim 1, wherein a water-absorption capacity of the physiological saline is 30 g/g to 90 g/g.

4. A method of producing a water-absorbent resin particle, comprising in the following order:
   a first polymerization step including obtaining a suspension containing a water-containing gelated polymer by polymerizing a water-soluble ethylenically unsaturated monomer in a suspension containing an oily liquid containing a hydrocarbon dispersion medium, a first aqueous liquid containing an aqueous solvent, the water-soluble ethylenically unsaturated monomer and a radical polymerization initiator, and a surfactant having an HLB value of 6 or higher, the first aqueous liquid being dispersed in the oily liquid; and
   a second polymerization step including mixing the suspension containing the water-containing gelated polymer at 45° C. or higher with a second aqueous liquid containing an aqueous solvent, a water-soluble ethylenically unsaturated monomer and a radical polymerization initiator, and polymerizing the water-soluble ethylenically unsaturated monomer in a suspension in which the second aqueous liquid is further dispersed.

5. The method according to claim 4, wherein in the second polymerization step, a temperature of the suspension in which the second aqueous liquid has been further dispersed at the time of completion of mixing of the suspension with the second aqueous liquid is 35° C. or higher.

6. The method according to claim 4, wherein in the first polymerization step, the oily liquid contains 50 parts by weight to 650 parts by weight of the hydrocarbon dispersion medium relative to 100 parts by weight of the water-soluble ethylenically unsaturated monomer contained in the first aqueous liquid.

7. A method of producing a water-absorbent resin particle comprising:
   a polymerization step including polymerizing a water-soluble ethylenically unsaturated monomer in a suspension containing an oily liquid containing a hydrocarbon dispersion medium, and an aqueous liquid containing an aqueous solvent and the water-soluble ethylenically unsaturated monomer, the aqueous solvent containing water, the aqueous liquid being dispersed in the oily liquid, wherein the aqueous liquid has a viscosity of 20 mPa·s or more at 20° C., and the suspension further contains a surfactant having an HLB value of 6 or higher.

8. The method according to claim 7, wherein the aqueous liquid further contains a water-soluble thickener, and the water-soluble thickener contains at least one type of compound selected from hydroxyalkyl celluloses, hydroxyalkyl alkyl celluloses and carboxyalkyl hydroxyalkyl celluloses.

9. A method of producing a water-soluble resin particle, comprising:

a polymerization step including polymerizing a water-soluble ethylenically unsaturated monomer in a suspension containing an oily liquid containing a hydrocarbon dispersion medium, and an aqueous liquid containing an aqueous solvent and the water-soluble ethylenically unsaturated monomer, the aqueous solvent containing water, the aqueous liquid being dispersed in the oily liquid, wherein the aqueous liquid further contains a hydrophilic polymeric dispersion agent, and the suspension further contains a surfactant having an HLB value of 6 or higher.

10. The method according to claim 9, wherein the hydrophilic polymeric dispersion agent contains at least one type of compound selected from the group consisting of polyvinyl alcohol, polyvinylpyrrolidone, polyethylene glycol, polypropylene glycol and polyglycerol.

11. The method according to claim 9, wherein the aqueous liquid contains 0.001 parts by weight to 10 parts by weight of the hydrophilic polymeric dispersion agent relative to 100 parts by weight of the water-soluble ethylenically unsaturated monomer.

12. The method according to claim 4, wherein the surfactant contains at least one type of compound selected from the group consisting of sorbitan fatty acid esters, polyglycerol fatty acid esters and sucrose fatty acid esters.

13. The method according to claim 4, wherein the water-soluble ethylenically unsaturated monomer contains at least one type of compound selected from the group consisting of acrylic acid and a salt thereof, methacrylic acid and a salt thereof, and acrylamide.

14. The method according to claim 4, wherein the hydrocarbon dispersion medium contains at least one type of compound selected from the group consisting of chain aliphatic hydrocarbons having 6 to 8 carbon atoms and alicyclic hydrocarbons having 6 to 8 carbon atoms.

15. The method according to claim 8, wherein the surfactant contains at least one type of compound selected from the group consisting of sorbitan fatty acid esters, polyglycerol fatty acid esters and sucrose fatty acid esters.

16. The method according to claim 9, wherein the surfactant contains at least one type of compound selected from the group consisting of sorbitan fatty acid esters, polyglycerol fatty acid esters and sucrose fatty acid esters.

17. The method according to claim 8, wherein the water-soluble ethylenically unsaturated monomer contains at least one type of compound selected from the group consisting of acrylic acid and a salt thereof, methacrylic acid and a salt thereof, and acrylamide.

18. The method according to claim 9, wherein the water-soluble ethylenically unsaturated monomer contains at least one type of compound selected from the group consisting of acrylic acid and a salt thereof, methacrylic acid and a salt thereof, and acrylamide.

19. The method according to claim 8, wherein the hydrocarbon dispersion medium contains at least one type of compound selected from the group consisting of chain aliphatic hydrocarbons having 6 to 8 carbon atoms and alicyclic hydrocarbons having 6 to 8 carbon atoms.

20. The method according to claim 9, wherein the hydrocarbon dispersion medium contains at least one type of compound selected from the group consisting of chain aliphatic hydrocarbons having 6 to 8 carbon atoms and alicyclic hydrocarbons having 6 to 8 carbon atoms.

* * * * *